US008067169B2

(12) United States Patent
Sahin et al.

(10) Patent No.: US 8,067,169 B2
(45) Date of Patent: *Nov. 29, 2011

(54) DETECTION OF MACROMOLECULAR COMPLEXES ON ULTRAFLAT SURFACES WITH HARMONIC CANTILEVERS

(75) Inventors: Ozgur Sahin, Cambridge, MA (US); Calvin F. Quate, Menlo Park, CA (US); Olav Solgaard, Stanford, CA (US); Henrik Persson, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 11/977,541

(22) Filed: Oct. 24, 2007

(65) Prior Publication Data
US 2009/0227040 A1    Sep. 10, 2009

Related U.S. Application Data

(63) Continuation-in-part of application No. 11/404,181, filed on Apr. 13, 2006.

(60) Provisional application No. 60/674,218, filed on Apr. 22, 2005.

(51) Int. Cl.
*C12Q 1/68* (2006.01)
*C12M 1/34* (2006.01)

(52) U.S. Cl. ..................... 435/6.1; 435/287.2

(58) Field of Classification Search .......... None
See application file for complete search history.

(56) References Cited

U.S. PATENT DOCUMENTS

| | | | |
|---|---|---|---|
| 5,345,815 A | | 9/1994 | Albrecht et al. |
| 5,763,768 A | | 6/1998 | Henderson et al. |
| 6,544,776 B1 | | 4/2003 | Gold et al. |
| 6,935,167 B1 | | 8/2005 | Sahin et al. |
| 7,089,787 B2 | * | 8/2006 | Sahin et al. .......... 73/105 |
| 7,302,833 B2 | | 12/2007 | Sahin et al. |
| 7,404,314 B2 | | 7/2008 | Sahin et al. |
| 7,451,638 B1 | * | 11/2008 | Sahin et al. .......... 73/105 |
| 2003/0215816 A1 | | 11/2003 | Sundararajan et al. |
| 2006/0005614 A1 | | 1/2006 | Sahin et al. |
| 2010/0120023 A1 | * | 5/2010 | Sahin et al. .......... 435/6 |

OTHER PUBLICATIONS

Guiducci et al. DNA detection by integrable electronics. Biosensors and Bioelectronics (2004) 19: 781-787.*
Castelino et al. Characterization of Grafting Density and Binding Efficiency of DNA and Proteins on Gold Surfaces. Langmuir (2005) 21: 1956-1961.*
Huang et al. Studies of Surface Coverage and Orientation of DNA Molecules Immobilized onto Preformed Alkanethiol Self-Assembled Monolayers. Langmuir (2000) 16: 3272-3280.*
Zhao et al. DNA-modified electrodes; part 4: optimization of covalent immobilization of DNA on self-assembled monolayers. Talanta (1999) 49: 751-756.*
Tian et al. Dynamic Microcantilever Sensors for Discerning Biomolecular Interactions. Analytical Chemistry (2005) 77: 1601-1606.*
Ozgur Sahin, "Harmonic Force Microscope: A new tool for biomolecular identification and material characterization based on nanomechanical measurements" (PhD thesis, Stanford University, 2006), 134 pages.*
Petrovykh et al. Quantitative Analysis and Characterization of DNA Immobilized on Gold. Journal of the American Chemical Society (2003) 125: 5219-5226.*
Robert W. Stark, et al., "Higher harmonics imaging in tapping-mode atomic-force microscopy," Review of Scientific Instruments, Dec. 2003, vol. 74, No. 12, 5111-5114.
Ozgur Sahin, et al., "High-resolution imaging of elastic properties using harmonic cantilevers," Sensors and Actuators A, 2004, 114:183-190.
Ozgur Sahin, et al., "Coupled Torsional Cantilevers for Label-free Single Molecular Level Bio-Detection and Nanomaterials Characterization," Solid-State Sensors, Actuators, and Microsystems Workshop, Hilton Head Island, South Carolina, Jun. 4-8, 2006.
Kawagishi, et al., "Mapping of lateral vibration of the tip in atomic force microscopy at the torsional resonance of the cantilever," Ultramicroscopy, 2002, vol. 91, 37-48.
Stanislaus S. Wong, et al., "Covalently functionalized nanotubes as nanometre-sized probes in chemistry and biology," Nature, Jul. 2, 1998, vol. 394, 52-55.
Nobuhiro Kato, et al., "Reduction in Feedback Bandwidth of the Force-Controlled Atomic Force Microscope Using a Polyimide Cantilever," Jpn. J. Appl. Phys., Nov. 11, 2001, vol. 40, 6594-6599.
Henrik H. J. Persson, et al., "Versatile Method for Chemical Reactions with Self-Assembled Monolayers of Alkanethiols on Gold," Langmuir, 2001, 17:3643-3650.
P.J. James, et al., "Interpretation of Contrast in Tapping Mode AFM and Shear Force Microscopy. A Study of Nafion," Langmuir, 2001, 17:349-360.
H. J, Kreuzer, et al., "Stretching a Macromolecule in an Atomic Force Microscope: Statistical Mechanical Analysis," Biophysical Journal, Jun. 2001, 80:2505-2514.
Oscar H. Willemsen, et al., "Simultaneous Height and Adhesion Imaging of Anti-body-Antigen Interactions by Atomic Force Microscopy," Biophysical Journal, Nov. 1998, 75:2220-2228.
J. Fritz, et al., "Translating Biomolecular Recognition into Nanomechanics," Science, Apr. 2000, 288:316-318.
Helen G. Hansma, "Varieties of imaging with scanning probe microscopes," PNAS, Dec. 1999, vol. 96, No. 26, 14678-14680.

(Continued)

*Primary Examiner* — Young J Kim
*Assistant Examiner* — Angela M Bertagna
(74) *Attorney, Agent, or Firm* — David J. Aston; Peters Verny, LLP

(57) ABSTRACT

Method and apparatus which uses harmonic cantilevers, such as used in atomic force microscopy, to detect variations in the attractive and repulsive forces on a solid surface as a result of macromolecular binding, for example, hybridization of a single stranded DNA molecule attached to the surface with another DNA molecule. The complexed macromolecule is less flexible than an uncomplexed molecule. It will typically have more negative charge due to amino acids or DNA monomers. Both stiffness of the surface and the attractive capillary forces will change after binding and may be detected. The present methods and materials enable ultraflat surfaces for the macromolecule deposition, and may include the use of a gold-coated mica substrate and a self-assembling monolayer.

4 Claims, 12 Drawing Sheets

OTHER PUBLICATIONS

Aleksandr Noy, et al., "Chemical Force Microscopy," Annu. Rev. Mater. Sci, 1997, 27:381-421.

Tommaso Auletta, et al., "b-Cyclodextrin Host—Guest Complexes Probed under Thermodynamic Equilibrium: Thermodynamics and AFM Force Spectroscopy," J. Am. Chem. Soc., 2004, 126:1577-1584.

Tai-Hsi Fan et al., "Analysis of Hydroynamic Intractions during AFM Imaging of Biological Membranes," Langmuir, 2003, 19:1347-1356.

S. John T. Van Noort, et al., "High Speed Atomic Force Microscopy of Biomolecules by Image Tracking," Biophysical Journal, Oct. 1999, 77:2295-2303.

Mario B. Viani, et al., "Probing protein—protein interactions in real time," Nature Structural Biology, Aug. 2000, vol. 7, No. 8, 644-647.

Ozgur Sahin, et al., "Resonant harmonic response in tapping mode atomic force microscopy," Physical Review B, 2004, 69, 165416-1 to 165416-9.

Marcel Margulies, et al,, "Genome sequencing in microfabricated high-density picolitre reactors," Nature, Sep. 2005, 437:376-380.

Kate Marusina, "Whole Genome Sequencing in 24 Hours," Genetic Engineering News, Sep. 2005, vol. 25, No. 15, 26-27.

Ming Su, et al., "Microcantilever resonance-based DNA detection with nanoparticle probes," Applied Physics Letters, May 2003, vol. 82, No. 20, 3562-3564.

* cited by examiner

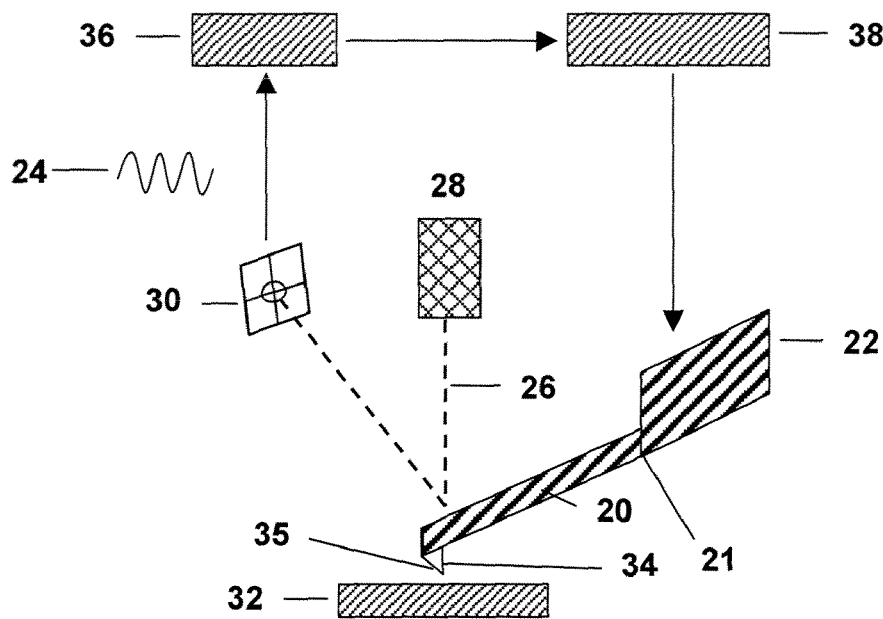
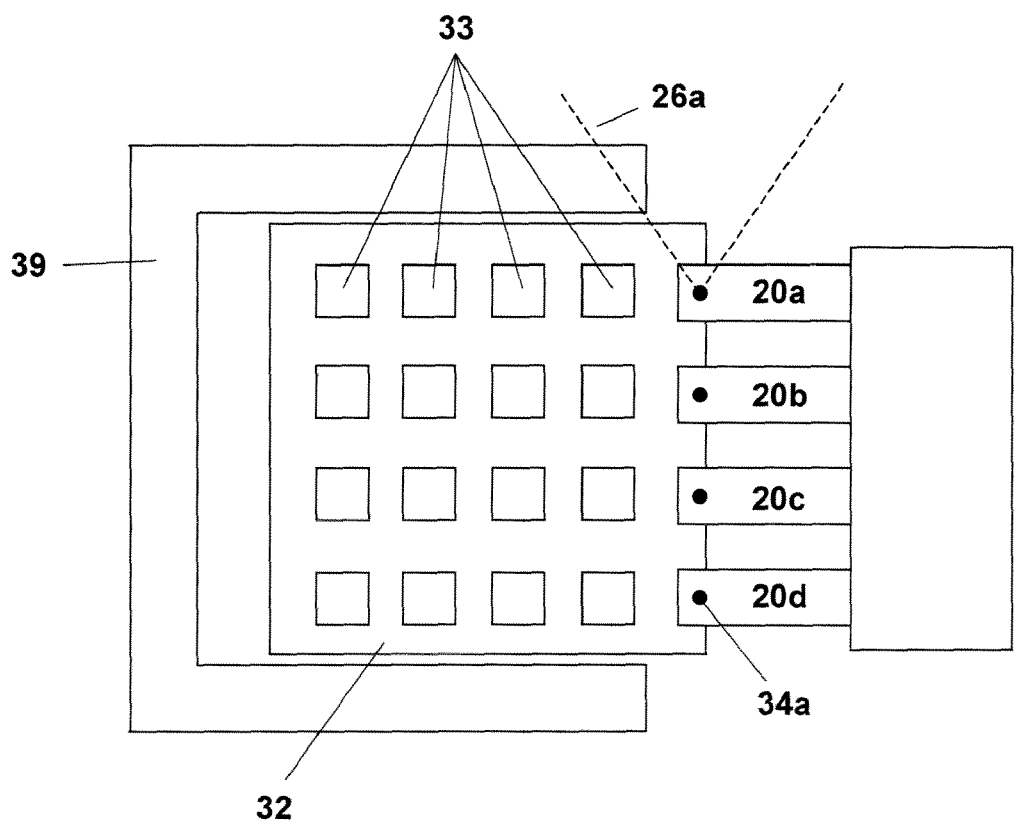
Figure 2

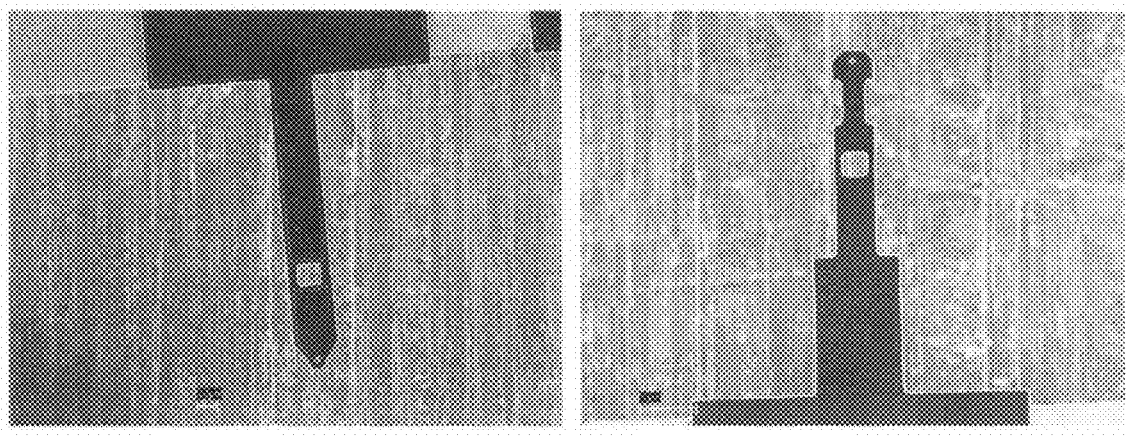
4A  4B
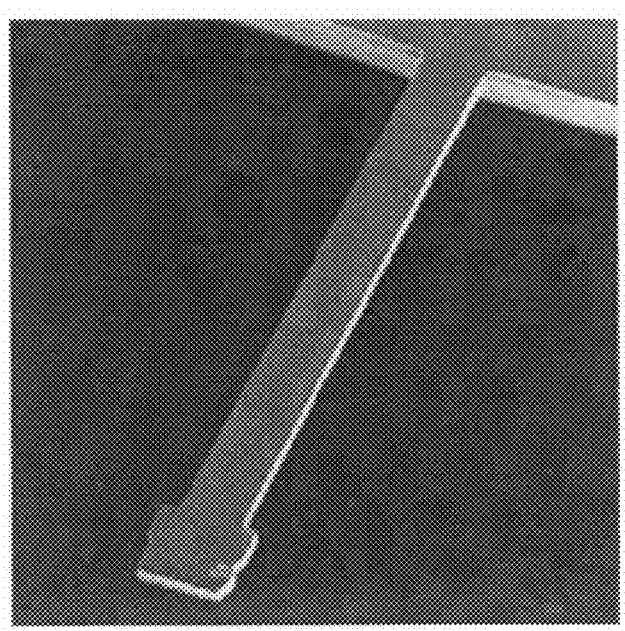
4C
Fig. 4 A-C

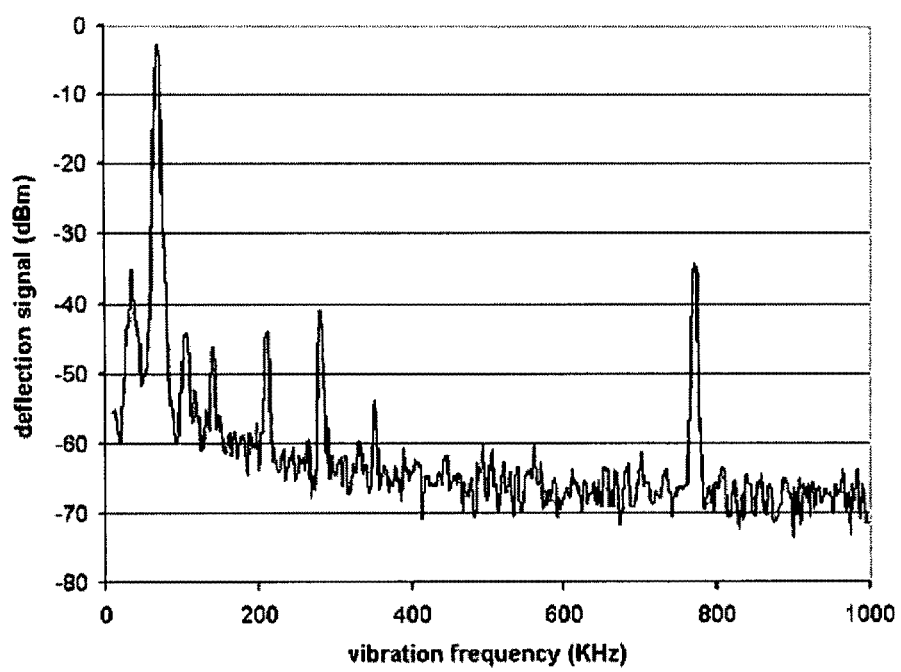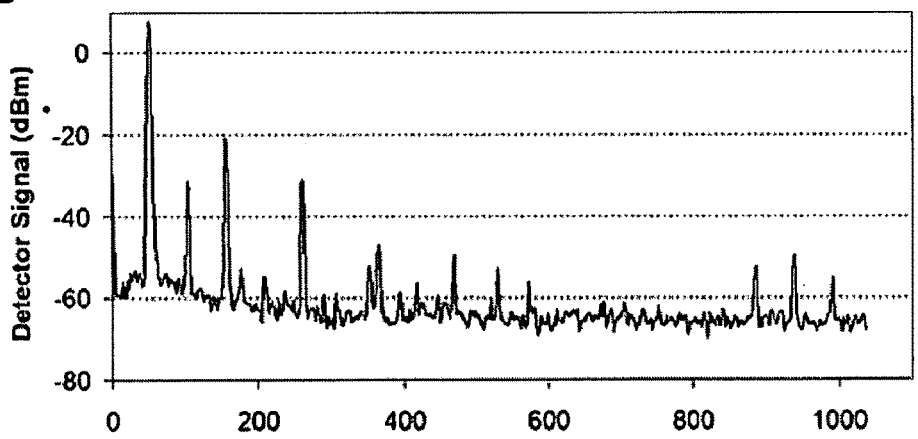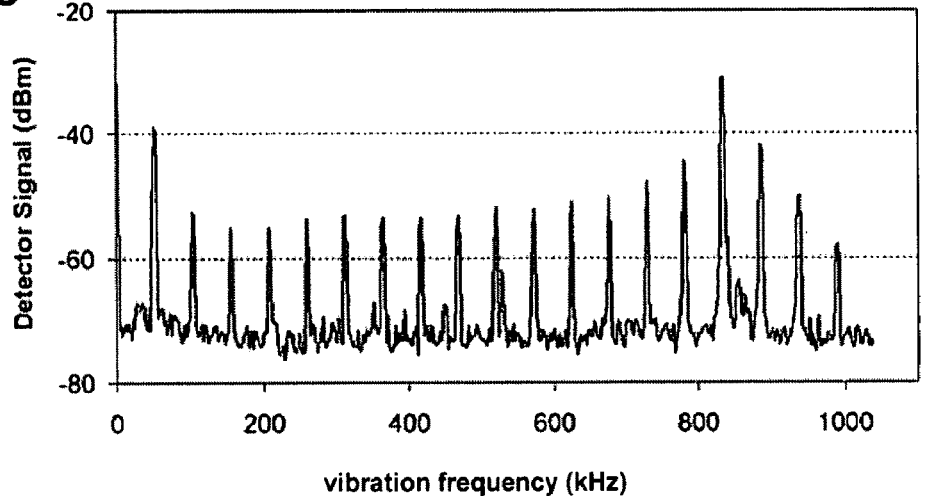
Fig. 5 A-C

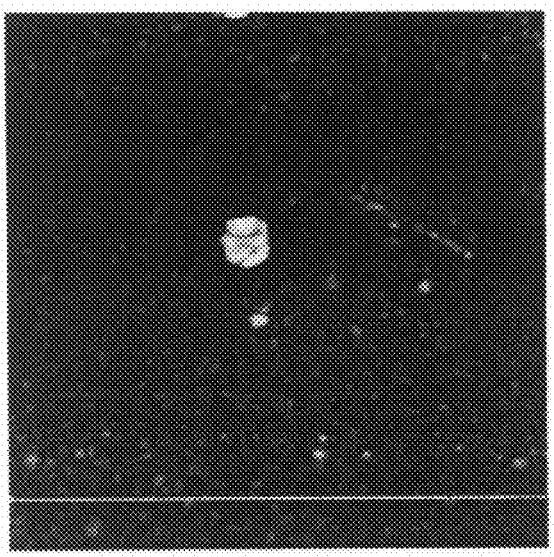
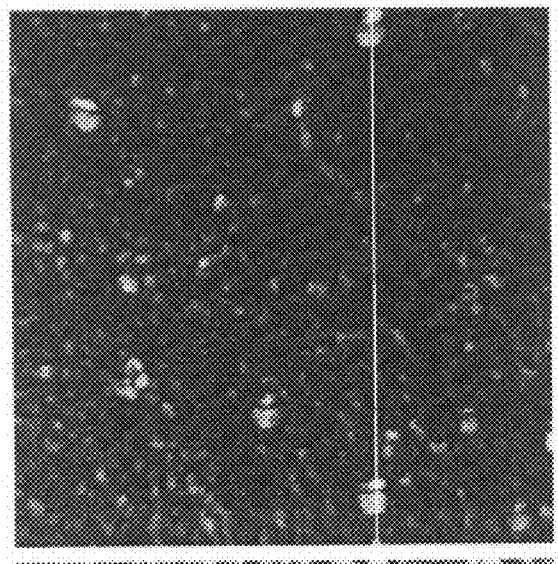
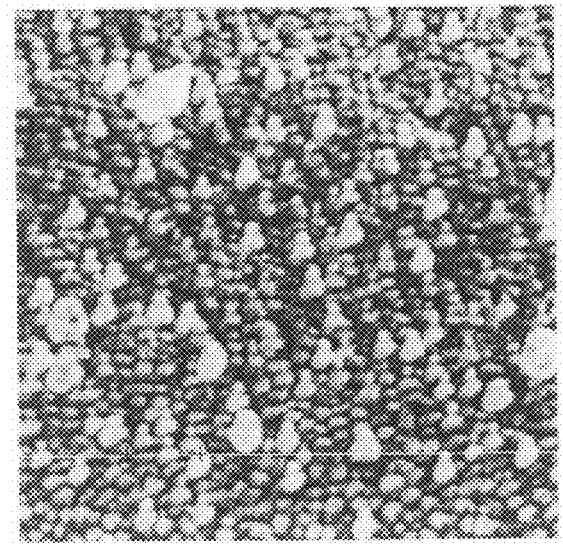
1.0 micron scan area
Fig. 7 A-C

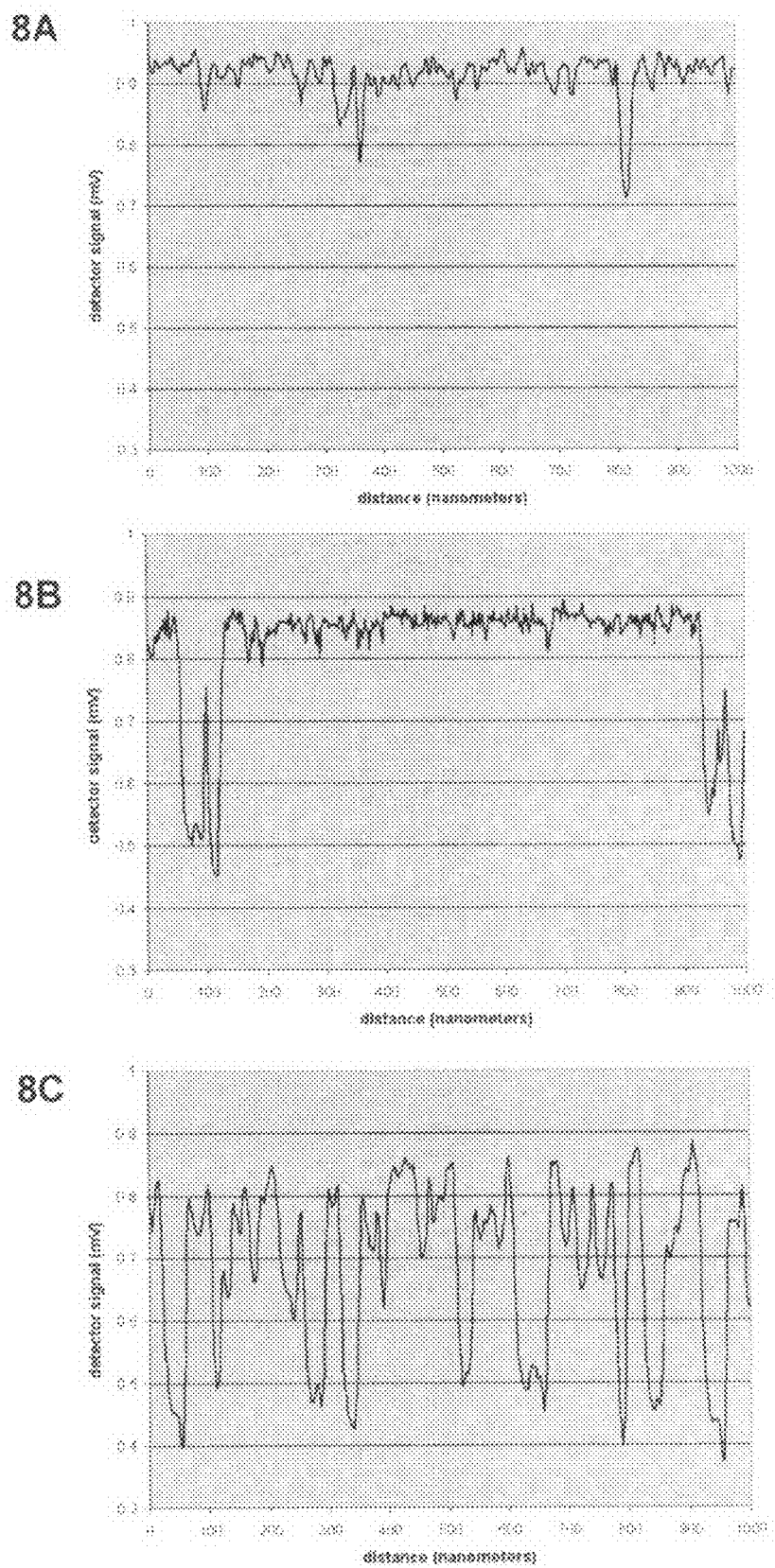
Fig. 8 A-C

10A
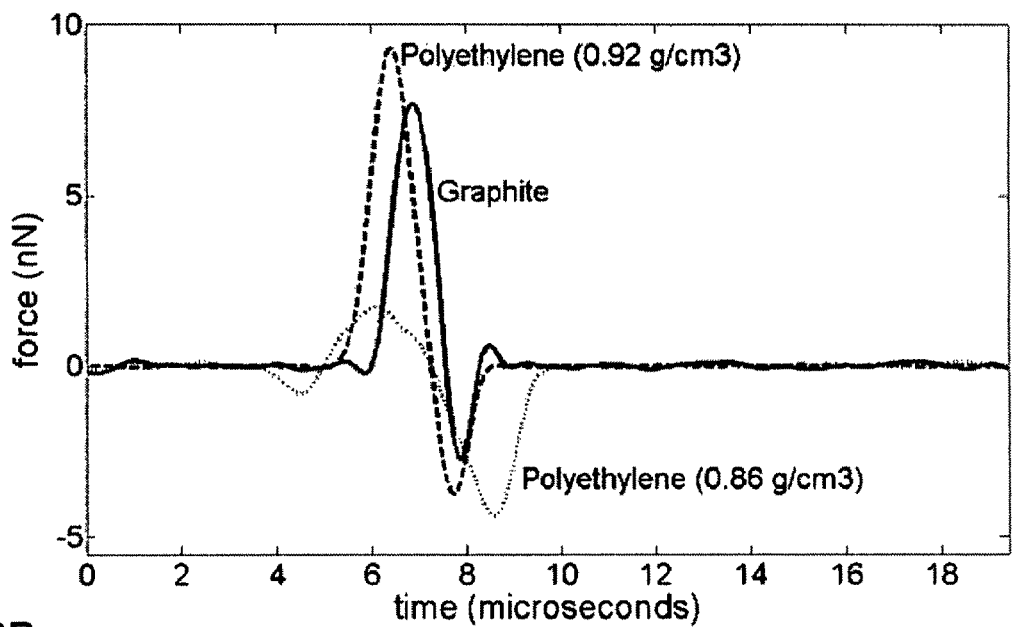
10B
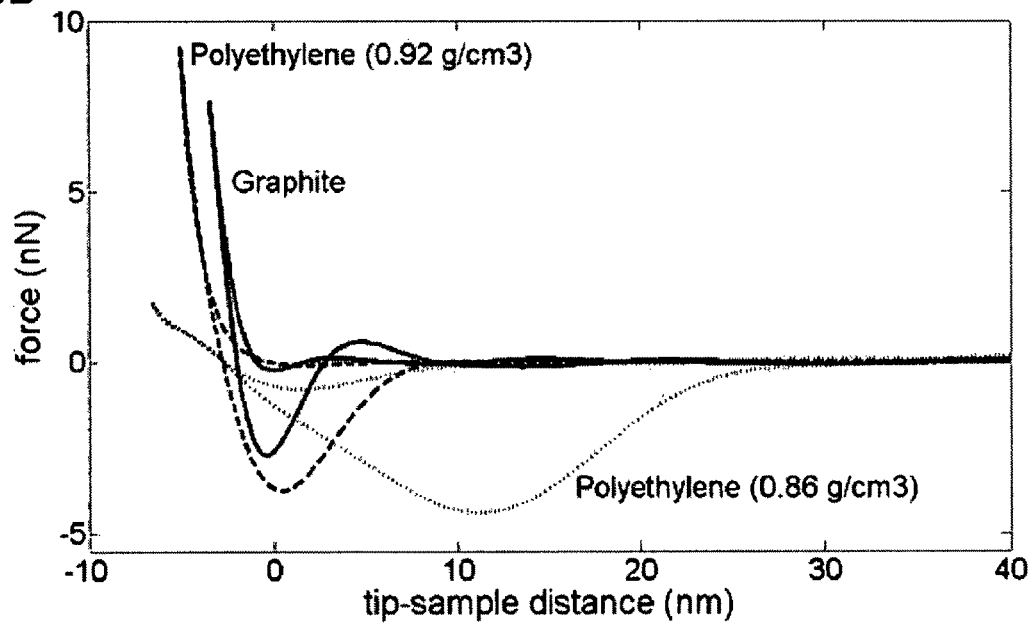
Fig. 10 A-B

DETECTION OF MACROMOLECULAR COMPLEXES ON ULTRAFLAT SURFACES WITH HARMONIC CANTILEVERS

CROSS-REFERENCE TO RELATED APPLICATIONS

This application claims priority from U.S. Provisional Patent Application No. 60/674,218 filed on Apr. 22, 2005 and U.S. application Ser. No. 11/404,181 filed Apr. 13, 2006, which are hereby incorporated by reference in their entirety.

STATEMENT OF GOVERNMENTAL SUPPORT

This invention was made not with U.S. Government support.

REFERENCE TO SEQUENCE LISTING, A TABLE, OR A COMPUTER PROGRAM LISTING COMPACT DISC APPENDIX

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to detection of the hybridization of DNA and other macromolecular events using scanning probe microscopy techniques, in particular, the use of harmonic cantilevers for tapping-mode atomic force microscope.

2. Related Art

Detection of hybridized DNA molecules has a central role in molecular biology and genetics. The hybridization reaction depends on the complementary matching of the sequence of single stranded DNA molecules. This allows one to use a single stranded DNA molecule with known sequence to identify the sequence of another DNA molecule. This fact has been widely used on DNA microarrays and similar technologies to determine the sequence of DNA molecules and to compare gene expression levels in different samples.

Atomic force microscopy (AFM) refers to a class of instruments and imaging methods where a sharp tip attached to the end of a flexible cantilever is scanned across a sample surface to map topographical features and various material properties. A variety of AFM is the tapping mode where the flexible cantilever is vibrated at one of its resonance frequencies in the vicinity of the sample. Vibration amplitude and other parameters of the cantilever motion are monitored to map the topography and material properties. The gentle interaction between the tip and the sample in tapping-mode AFM has made it the dominant operation modality of AFM.

Harmonic cantilevers and coupled torsional cantilevers for tapping-mode atomic force microscopy are specially designed cantilevers that can be used as a replacement for conventional cantilevers. When used in tapping mode, these cantilevers provide additional vibrational signals at higher frequencies (harmonics) that depend on the forces between the sample and the sharp tip of the AFM. These tip-sample forces have attractive components due to capillary forces and Van der Waals forces, and repulsive components due mainly to the stiffness of the sample. A detailed description of this technique can be found in Sahin, O., Yaralioglu, G., Grow, R., Zappe, S. F., Atalar, A., Quate, C. F. & Solgaard, O., "High resolution imaging of elastic properties using harmonic cantilevers," *Sensors and Actuators A*, 114, 183-190 (2004); and Sahin, O., Atalar, A., Quate, C. F. & Solgaard, O., "Resonant harmonic response in tapping-mode atomic force microscopy," *Phys. Rev. B.* 69 165416 (2004).

Kreuzer, et al., "Stretching a Macromolecule in an Atomic Force Microscope: Statistical Mechanical Analysis," *Biophys. J.* 80: 2502-2524 (2001) discloses methods for calculating a force-extension curve for a given macromolecule, as theoretically modeled for a molecule of PEG.

Antognozzi, et al., "Interpretation of Contrast in Tapping Mode AFM and Shear Force Microscopy: A Study of Nafion," *Langmuir* 17:349-360 (2001) discloses the use of tapping mode AFM for imaging delicate samples. The publication describes the use of shear-force microscopy (SHFM). The probe is mounted on a piezoelectric actuator, which drives the probe at a frequency close to one of its resonant modes. The tip is mounted in such a fashion that its direction of vibration is parallel to the sample surface, as the probe comes into close proximity with the sample, ~10 nm. the amplitude of oscillation decreases due to damping from the Van der Waals interactions. NAFION™ is a commercially available perfluorosulfonate cation-exchange membrane (CEM) manufactured by E I du Pont de Nemours & Co. Inc. The two complementary scanning probe microscopy (SPM) techniques of AFM and TDFM were used to investigate the difference in phase contrast exhibited by two NAFION™ samples differing only in cation from (H+ and Cs+).

Auletta, et al., "A-Cyclodextrin Host-Guest Complexes Probed under Thermodynamic Equilibrium Thermodynamics and AFM Force Spectroscopy," *J. Am. Chem. Soc.* 126: 1577-1584 (Jan. 15, 2004) discloses the use of "chemical force microscopy," which combines the resolution available through force microscopy with attractive/repulsive forces taking place between a functionalized probe tip and the sample, allowing compositional mapping of surfaces with different chemical functionalities on the basis of different adhesion properties. The publication presents a study of single host-guest (HG) complex rupture forces between β-cyclodextrin self-assembled monolayers (SAMs) and several guest molecules confined onto the surface of gold-coated AFM tips by adsorption in mixed SAMs.

Viani, et al., "Probing protein-protein interactions in real time," *Nature Struct. Biol.* 7:644-647 (2000) discloses the use of a small cantilever AFM to observe individual protein interactions. The authors observed, in real time, individual *Escherichia coli* GroES proteins binding to and then subsequently dissociating from individual *E. coli* GroEL proteins. Height fluctuation (topography), rather than stiffness was measured.

Van Noort, et al., "High Speed Atomic Force Microscopy of Biomolecules by Image Tracking," *Biophys. J.* 77:2295-2303 (1999) discloses an image-tracking procedure to zoom in on an individual DNA plasmid. A stand-alone AFM was used. Triangular Si3N4 cantilevers (Park Scientific, Sunnyvale, Calif.) with a spring constant of 0.5 N/m were used for tapping mode in liquid, at a frequency of 30 kHz, non-harmonic mode.

Willemsen, et al., "Simultaneous Height and Adhesion Imaging of Antibody-Antigen Interactions by Atomic Force Microscopy," *Biophys. J.* 75:2220-2228 (1998) discloses imaging of individual ICAM-1 antigens in both tapping mode and adhesion mode. The contrast in the adhesion image that was measured simultaneously with the topography was reportedly caused by recognition between individual antibody-antigen pairs. By comparing the high-resolution height image with the adhesion image, it was shown that specific molecular recognition is highly correlated with topography. V-shaped cantilevers (MICROLEVERS, tip F, Park Scientific Instruments, Sunnyvale, Calif.) with a spring constant of 500 pN/nm were operated at frequencies between 18 and 24 kHz.

Further reports are: Hansma, H. G., K. A. Browne, M. Bezanilla, and T. C. Bruice, 1994. "Bending and straightening of DNA induced by the same ligand: characterization with the atomic force microscope,' *Biochemistry*, 33:8436-8441; Hansma, H. G., I. Revenko, K. Kim, and D. E. Laney, 1996, "Atomic force microscopy of long and short double-stranded, single-stranded and triple-stranded nucleic acids," *Nucleic Acids Res.* 24:713-720; and Laney, D. E., R. A. Garcia, S. M. Parsons, and H. G. Hansma, 1997, "Changes in the elastic properties of cholinergic synaptic vesicles as measured by atomic force microscopy," *Biophys. J.* 72:806-813.

BRIEF SUMMARY OF THE INVENTION

The following brief summary is not intended to include all features and aspects of the present invention, nor does it imply that the invention must include all features and aspects discussed in this summary.

The present invention uses harmonic cantilevers to detect variations in the attractive and repulsive forces on a solid surface as a result of the hybridization or other structural change of a macromolecule such as a single stranded DNA molecule attached to the surface complexed with itself or another macromolecule such as another DNA molecule. These are referred to generally as tip-sample forces, as distinguished from other types of measurements, such as topographical measurements. These forces can be measured by detecting changes in tip vibrational amplitude or frequency changes (phase).

Thus the present methods and apparatus provide a system whereby changes in one or both of amplitude and phase in said frequency indicate a complexed versus a non-complexed macromolecule. Thus, the method utilizes data acquisition involving standard measurements of cantilever movement as illustrated in Section 5 below. However, in the present case, by measuring cantilever movement and frequency, one may calculate force by Hook's law, $F=-K \times d$, where F=force, K is a constant and depends on the material and dimensions of the cantilever and D is the motion of the cantilever.

In one aspect, the present invention is a method for distinguishing macromolecular binding, wherein macromolecules are disposed on discrete locations on a substrate, comprising the steps of vibrating a harmonic cantilever with a tip and obtaining a frequency signal from said vibrating; contacting a vibrating harmonic cantilever tip with said macromolecules at said discrete locations; measuring changes in said measured frequency (or multiple frequencies, or direct temporal waveform of high frequency vibrations) at different macromolecules at different discrete locations; and measuring changes in one or both of amplitude and phase in said frequency in order to distinguish a complexed from a non-complexed macromolecule. The method of the invention preferably employs atomic force microscopy, but other forms of microscopy (e.g., scanning tunneling microscopy), which use a vibrating, harmonic cantilever with a tip, can be used. The present inventive method further comprises the step of contacting a vibrating harmonic cantilever tip with the macromolecules at various, predetermined locations. The macromolecules may be in a complexed or non-complexed state, and the probe is scanned across the sample substrate, in a known manner, to contact various macromolecules. Typically, the present device will use AFM comprising a sharp probe moving over the surface of a sample in a raster scan. However, devices may also be designed in which the sample is moved relative to a cantilever vibrating in a fixed position. The present invention also includes embodiments using use of coupled torsional cantilevers.

In certain aspects of the invention, the cantilever is operated in tapping mode in air or other gases, and the cantilever is oscillated at its resonant frequency (preferably 10 kHz to 10 MHz, more preferably 10 to 700 kHz) and positioned above the surface so that it only taps the surface for a very small fraction of its oscillation period. In certain aspects of the present invention, multiple harmonic frequencies are measured simultaneously.

In other aspects of the invention, the tip is vibrated at or near a fundamental frequency. The vibrating is within 10% of a fundamental frequency between 10 and 700 kHz and said signal is from a harmonic having a detection signal to noise ratio of at least 10 dB in a 1 kHz measurement bandwidth, preferably the tip will be vibrating is within 3% of its fundamental frequency.

The substrate material may be any rigid inert material, and may be further configured to contain wells for liquid samples. It may be, for example, silicon, quartz, glass, ceramic, carbon, plastic, or metal.

The vibrating of the cantilever may be at a fundamental frequency between 10 and 700 kHz. One or more (up to about 20) harmonics of the fundamental frequency may be measured, as long as the harmonic frequency has a sufficient signal to noise ratio. As disclosed below, the signal can be obtained from a harmonic having a detection signal at least 10 dB, even 20 dB, over a signal generated at the fundamental frequency. This detection signal will be measured within a 1 kHz bandwidth. It has been shown to be advantageous to measure a harmonic between a second and $20^{th}$ harmonic, or between an eighth and a $16^{th}$ harmonic. Good harmonic signals were obtained with the cantilever having a spring constant of about 1N/m and a quality factor between 70 and 80.

Since the tip may have to scan a large area of multiple macromolecular samples, it is desirable in some aspects to have a tip is between 30 nm and 100 nm across. It is not necessary in all applications to distinguish individual macromolecules, such as when looking for a hybridization reaction in a sample suspected of containing a complementary nucleic acid.

In some applications, the scanning may be done while a reaction is taking place, or for detecting a native protein, which should not be dried. In this case, the contacting of the cantilever tip with said macromolecule occurs in a liquid.

The present apparatus may further comprise a plurality of cantilevers for contacting different regions of the sample substrate and a receptacle for receiving said sample substrate in a predetermined orientation for scanning.

Certain aspects of the present invention involve a novel apparatus. In this aspect, the apparatus comprises a harmonic cantilever having a tip which is treated to minimize chemical sample interaction, e.g., made hydrophobic or hydrophilic; a mechanism for vibrating a harmonic cantilever such that the tip contacts a sample substrate at a certain pre-selected frequency (the fundamental frequency); a mechanism for moving the tip relative to the sample substrate so as to contact a plurality of discrete locations which may contain discrete macromolecules fixed on the substrate sample, where said sample will have thereon macromolecules in different complex bonding states; a detector circuit for detecting changes in cantilever vibration frequency caused by differences in complex bonding states between macromolecules on the sample substrate and a detector circuit, which may comprise a lock-in amplifier locked onto a particular harmonic frequency, or high frequency analog to digital converter (harmonic amplitude/phase and time resolved forces can be calculated by computer afterwards). The detector circuit will comprise a circuit for measuring or obtaining a signal at a certain frequency that is a multiple of at least two of the fundamental vibration frequency of the cantilever.

The detector circuit is responsive to cantilever movement, such as torsional bending of coupled torsional cantilevers, like a quadrant photo-detector. The device will further comprise an output device for showing changes in frequency vibration for discrete locations on the sample substrate representative of different macromolecules.

The tip may be fabricated from a number of materials, including carbon, e.g., graphite or diamond.

BRIEF DESCRIPTION OF THE DRAWINGS

FIG. 2 is a generalized schematic drawing of a tapping-mode atomic force microscope(A) and a multi-cantilever embodiment(B);

FIG. 4A is micrograph showing a top view of a harmonic cantilever that enhances vibration signals at the $16^{th}$ harmonic; FIG. 4B is a micrograph showing a top view of a harmonic cantilever that enhances vibration signals at the $11^{th}$ harmonic; FIG. 4C is a micrograph showing a coupled torsional cantilever, with an offset location of the sharp tip;

FIG. 5A is a plot of the vibration spectrum of the cantilever shown in 3B while tapping on a sample; FIG. 5B is a plot of a measured flexural vibration spectrum; FIG. 5C is a plot of a measured vibration spectra of a coupled torsional cantilever shown in FIG. 4C tapping on a polystyrene sample;

FIG. 7 is a series of images obtained by the harmonic cantilever on three surfaces, where FIG. 7A shows a surface with only single stranded molecules attached to it; 7B shows a surface which has both single and double stranded DNA molecules attached, however double stranded molecules are approximately 0.1% of all the DNA molecules; FIG. 7C shows a surface which has mostly double stranded molecules attached to it;

FIG. 8 A-C shows the measured vibration signal levels across a section of the corresponding images in FIG. 7A-C;

FIG. 10 is a plot of (a) time-resolved tip-sample forces measured with coupled torsional cantilever on three materials; and (b) the same measurements in (a) are plotted against tip-sample separation;

DETAILED DESCRIPTION OF THE PREFERRED EMBODIMENT

1. Introduction

Figure 1:
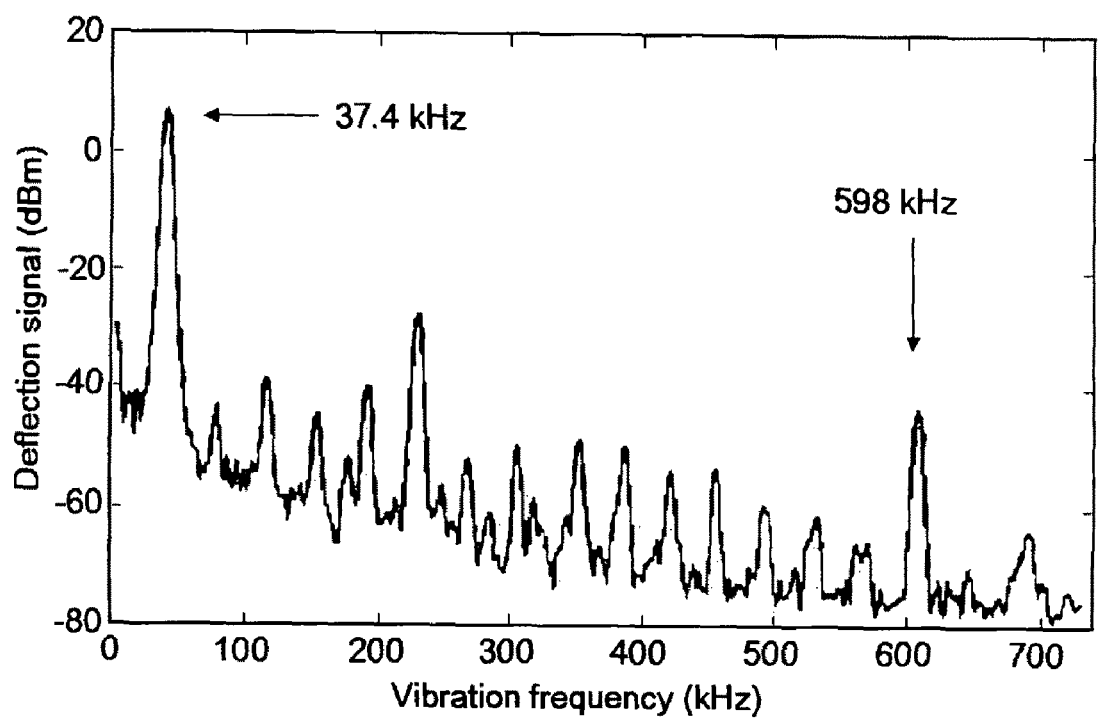
FIG. 1 is a plot of a vibrational spectrum of a harmonic cantilever.

At the molecular scale, chemical properties are largely coupled to the mechanical properties. Formation of a chemical bond within a molecule or between molecules not only alters the electrical or optical properties but it also changes the mechanical properties of the molecules. Biological reactions like DNA hybridization, protein folding and substrate binding result in structural and mechanical changes within the molecules. In crystalline materials such as those used for semiconductor processes, the local mechanical properties are highly affected by the defects within the crystal or by the formation of thin-films at the surfaces. In novel materials such as carbon nanotubes, the changes in physical dimensions that result in variations in electrical and optical properties also affect the mechanics of the molecules or nanostructures. It is therefore very attractive to use mechanical properties of molecules to detect biochemical reactions.

Some of the applications of this technology include the readout of DNA microarrays and protein arrays, whereby binding of a sample molecule to the array probe can be detected, imaged and quantified. In the field of DNA sequencing, a device according to the present invention has the potential to reduce the cost of microarrays and readers by 1-2 orders of magnitude.

In previous tapping AFM methods, information regarding the stiffness of the surface is inherently transferred to higher order mechanical modes of the cantilever. Unfortunately, the information is not used and is often lost due to low mechanical response of the cantilever at those frequencies. Described below is a method that uses a modification in the cantilever geometry that enhances the signals at those frequencies. This geometric modification tunes a higher order flexural resonance frequency to an integer multiple of the fundamental resonance frequency. This condition enhances (2 orders of magnitude) the cantilever response and recovers the information regarding the stiffness of the surface. This cantilever is fabricated by following the same process steps that are used for commercial AFM cantilevers. This cantilever (called the harmonic cantilever) was tested by recording its vibration spectrum in AFM operation. The spectrum is given in FIG. 1. As indicated by the arrow, a sensitive detection signal is present as amplitude signals from deflection of the cantilever at the 16th peak, at 598 kHz. This peak is about 20 dB higher than its neighbors, demonstrating the enhancement of the signal at that particular harmonic. The amplitude of that peak is related to the stiffness of material under investigation. The spectrum in FIG. 1 was generated from contact of the tip with a sample comprising a silicon wafer with native oxide.

It has now been found that a double stranded (hybridized) DNA molecule is less flexible than a single stranded DNA. It also has more negative charge due to the negatively charged DNA backbones. While not wishing to be bound by any scientific theory, the cantilever response is thought to vary because of differences in the stiffness of the surface and the attractive capillary forces, which occur after hybridization. Tip-sample forces in tapping-mode AFM will be different when the cantilever is tapping on a surface with a single stranded DNA attached and when it is tapping on a surface with a double stranded (hybridized) DNA attached. Therefore, the signals on double stranded DNA molecules will be different than the signals on single stranded molecules. By scanning the harmonic cantilever across a surface with DNA molecules attached in tapping-mode and by recording the signals at the high frequency vibrations provided by harmonic cantilever, this invention detects and quantifies the hybridized molecules on a surface.

The term "harmonic cantilever" is used here in a general sense, to include harmonic cantilevers such as shown in 6,935,167 (discussed below), coupled torsional cantilevers, and other cantilevers useful in scanning probe microscopy which are designed and coupled with instrumentation to obtain data from high frequency vibrations in dynamic force microscopy. The use of a harmonic cantilever facilitates imaging of elastic properties through enhanced higher harmonic imaging.

The term "complexed" as used herein refers generally to a molecular change that involves chemical bonds within the macromolecule being studied, or between that macromolecule and another molecule to be bound to it. It is necessary only that the binding affects the stiffness of the molecule, which is demonstrated in several examples below.

As stated, the invention comprises a method for distinguishing macromolecular binding. The term "macromolecular binding" refers to macromolecules which have bound to complementary molecules such as polynucleic acid hybridization, protein binding (e.g., complexes such as antibody-antigen, receptor-ligand, enzyme-substrate, enzyme-inhibitor), protein-DNA complexes and intramolecular binding such as folded vs. denatured RNA, DNA and proteins, and thermoplastic polymers which are treated chemically or physically to alter stiffness. In the latter case, the stiffness of the macromolecule is modified by the existence intramolecular bonds (H-bonding, disulfide linkages, etc.) and forces when the protein/macromolecule is folded.

Coupled torsional cantilevers contemplated by the present invention have an asymmetric shape with an offset tip. When used in tapping-mode tip-sample forces excite the torsional modes through higher harmonic generation. Because the width of the cantilever is much smaller than its length a small tip displacement due to torsional bending will generate a larger angular displacement compared to flexural modes. The torsional vibrations can be measured with regular four quadrant position sensitive photo-detectors that are commonly used in atomic force microscopes. When a higher harmonic matches with a torsional resonance frequency the vibrations at that harmonic will be resonantly enhanced because of the large quality factors of the torsional modes (~1000). This cantilever provides enhanced signals at a number of harmonic frequencies of torsion (up to eight or more), as well as of flexural movement.

As described below, it has been found that changes in one or both of amplitude and phase in said frequencies (particularly higher harmonic frequencies) indicate a complexed versus a non-complexed macromolecule. Each frequency has an amplitude and phase value associated with it, including the fundamental. In this case, we are detecting the amplitudes and phases at frequencies above the fundamental. These are the higher harmonic frequencies. One or multiple harmonics can be measured simultaneously via coupled torsional cantilevers.

DNA hybridization, for example, changes various chemical and physical (e.g., optical and mechanical) properties of the molecule. As disclosed in Viani, et al., "Probing protein-protein interactions in real time," supra, upon hybridization on a surface (like in the self assembled monolayer of the publication), an in-plane mechanical stress (or a relief in stress) occurs.

In contrast to previous work (e.g., Viani, et al., supra), the mechanical effect has been found now to be much more significant in the out of plane direction (vertical to the surface). In order to measure that effect, one applies force to the molecule on the surface vertically and measures the response of the molecule. A scanning probe microscope (SPM) has the desired property to do this type of an experiment. The tip of the SPM will squeeze the molecule and the response of the molecules will depend on whether they are single or double stranded. The response of the molecule is determined with the use of Harmonic Cantilevers or Coupled Torsional Cantilevers. As described below, it has now been found that this change is significant enough to be detected. As is known in the art, SPM includes a family of microscopes that may be adapted for use according to the present teachings. This family of microscopes includes (1) Scanning Tunneling Microscope—STM; (2) Atomic Force Microscope—AFM, (3) Force-Modulated AFM, (4) Lateral Force Microscope—LFM, (5) Magnetic Force Microscope—MFM, (6) Scanning Thermal Microscope—SThM, (7) Electrical Force Microscope—EFM and (8) Near-field Scanning Optical Microscope—NSOM.

There are multiple parameters affecting the interaction between the molecules and the tip of the probe. Capillary forces are an example of that. These can also be different on a single stranded vs. double stranded. Also the effect of the stiffness of the substrate will reflect onto the measurements. For example, when tapping on a single stranded molecule, forces due to the single stranded molecule could be so small that we are effectively interacting with the substrate. Conversely, a double stranded molecule could be able to supply the force to stop the tip motion and turn it back. This will affect the contrast in an advantageous way.

2. Overview of Device

Figure 3:
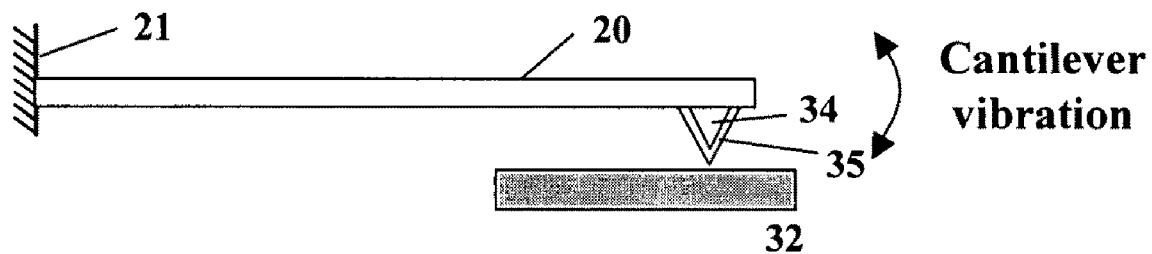
FIG. 3 is a schematic drawing of a cantilever tapping on a sample.

An overview of the device is shown in FIGS. 2 and 3. These figures illustrate an embodiment using harmonic cantilevers in tapping-mode AFM. AFMs can generally measure the vertical deflection of the cantilever with picometer resolution. To achieve this, most AFMs today use the optical lever, a device that achieves resolution comparable to an interferometer while remaining inexpensive and easy to use. The optical lever operates by reflecting a laser beam off a vibrating cantilever. Angular deflection of the cantilever causes a twofold larger angular deflection of the laser beam. The reflected laser beam strikes a position-sensitive photodetector consisting of two side-by-side photodiodes. The difference between the two photodiode signals indicates the position of the laser spot on the detector and thus the angular deflection of the cantilever.

Referring now to FIG. 2A, a flexible cantilever 20, which is fixed at the base 21 and free at the other end, is vibrated on or near its resonance frequency. The cantilever is vibrated with a piezo-element 22 attached to the base of the cantilever. The deflections of the cantilever are monitored with a laser beam 26 from laser 28 reflecting from the back of the cantilever near the tip end and falling onto a position sensitive detector 30, which is a split photodetector. A split detector has two or more separate parts, giving two voltage outputs, depending on the angle of the reflected light, which in turn depends on the deflection of the cantilever.

When the cantilever 20 is brought to the close vicinity of the surface of the sample 32, the sharp tip 34 attached to the free end interacts with the surface and the vibration amplitude of signal 24 reduces. The tip 34 has an outer surface 35 with predetermined sample adhesion, preferably in the form of a thin, preferably monolayer, coating of a hydrophobic compound such as a silane, or, alternatively, a hydrophilic polymer. The choices of tip surface will depend on the sample to be analyzed, in that hydrophilic biomolecules will indicate use of a hydrophobic surface. An amplitude detector 36 receives the signal from the photodetector 30 showing a change in voltage as a result of the change in cantilever amplitude. The amplitude detector 36 provides a signal representative of the amplitude and frequency of vibration of the cantilever. The detector 36 comprises a split photodetector and may comprise a detection mechanism sensitive to torsional bending of coupled torsional cantilevers, like a quadrant photo-detector.

More importantly, the detector circuit can measure or calculate higher included frequencies (harmonics) of the cantilever vibrations. That is, although the cantilever is vibrated at a single (fundamental) frequency, higher order signals representative of different multiples of this frequency are measured. This provides the potential to image material properties such as stiffness, viscoelasticity or capillary forces.

The detector circuit may comprise a lock-in amplifier locked onto a particular harmonic frequency, or high frequency analog to digital converter (harmonic amplitude/phase and time resolved forces can be calculated by computer afterwards).

Commercial detector equipment is available. For example, Nanoscience Instruments sells an easy PLL Sensor Controller and digital FM Detector for scanning probe microscopy applications such as UHV AFM, MFM, and NSOM. The Sensor Controller provides the oscillation circuit to drive the AFM sensor (cantilever or tuning fork) at its resonance frequency. The Digital FM detector provides frequency detection. The modules can be used together or separately as stand-alone modules.

Further design guidance, which is similar to the present design, but may be adapted as needed, is given in Stark et al. "Higher harmonics imaging in tapping-mode atomic-force microscopy," *Review of Scientific Instruments* 74(12) 5111-5114 (2003). The bandwidth should be limited to fc of about 50 kHz by a photodiode preamplifier. Thus signals are damped by a factor of 10 at f=500 kHz due to the low pass characteristics of the electronic circuit. The signals are demodulated by a lock-in amplifier ~EG&G 5302, EG&G Inc., Princeton with a time constant of 100 µs. The lock-in amplifier output (x, y) is transformed into polar coordinates (r, Φ) by dedicated converter electronics. The signal amplitude r is used for AFM feedback. An external function generator (DS 345, Stanford Research) may be used for the generation of the AFM driving signal. A second lock-in amplifier (SR 844, Stanford Research Systems) is used for the detection of the higher harmonic signals. The reference signal is generated with a second function generator of the same type. To maintain phase stability both function generators are coupled by a 10 MHz frequency standard. This separates detection of the fundamental and the harmonic frequency assures that only higher harmonics of the AFM signal are detected avoiding possible generation of harmonics due to the signal mixing in the lock-in amplifier.

This operates with a feedback controller 38, which adjusts the height of the cantilever base 21 in order to maintain the vibration amplitude at a set-point value (set-point amplitude). When the cantilever is scanned across a surface, the feedback signal reflects the topography of the surface. The vibration amplitude is typically 10-100 nanometers.

Referring now to FIG. 2B, the sample substrate 32 may be seen in top view to comprise a plurality of samples 33. A receptacle 39 is provided to receive a standard size sample (e.g., DNA chip) for a predetermined scanning pattern. In order to increase sample processing, a number of cantilevers 20*a*, 20*b*, 20*c* and 20*d* are shown. The number of cantilevers may be chosen to match a standard sample array, e.g., with the number of cantilevers matching the number of sample rows. Each cantilever has a tip 34, 34*a* and is vibrated in a similar frequency and amplitude, so that signals from each cantilever are comparable. The cantilevers are operated at a set amplitude, and the tips are similarly coated. Each cantilever has its own laser detector beam, as shown at 26*a*. This arrangement may be used, for example in a DNA sequencing chip, where the DNA is hybridized to an immobilized probe, and individual nucleotides are added in the presence of DNA polymerase and other reagents so that polymerization occurs if the proper nucleotide is added. The cantilever can scan along the sample and detect nucleotide incorporation. A computer memory stores data from each cantilever according to each location.

3. Harmonic Cantilever

As shown in FIG. 3, a harmonic cantilever includes a cantilever arm 20 having a fixed end 21 and a free end and a probe tip 34 projecting from the cantilever arm near the free end. The cantilever arm has a fundamental resonance frequency at a fundamental mode and at least one higher order resonance frequency and the cantilever arm has a shape selected to tune the fundamental resonance frequency or a resonance frequency of a selected higher order mode so that the resonance frequency of the selected higher order mode and the fundamental resonance frequency has an integer ratio. The fundamental resonance frequency or the resonance frequency of the selected higher order mode of the cantilever can be tuned by introducing geometric features to specific locations of the cantilever arm. The geometric features operate to modify the effective spring constant and/or the effective mass of the cantilever, thereby modifying the resonance frequency of the desired mode (the fundamental mode or a higher order mode). For example, the fundamental resonance frequency of the cantilever may be tuned by selecting a specific shape for the cantilever arm. In taping mode AFM, the cantilever is vibrated at its fundamental resonance frequency with sufficiently large amplitudes (10-100 nm) to avoid sticking to the sample surface. The distance between the sample surface 32 and the rest position of the tip is kept shorter than the free vibration amplitude so that tip hits the surface once every period. Therefore, the amplitude of the cantilever vibration is reduced to the tip-sample separation. The duration of the intermittent contacts can be as long as 15% of the oscillation period, depending on the hardness of the sample. Further details on the design of a harmonic cantilever are given in "Harmonic cantilevers and imaging methods for atomic force microscopy," U.S. Pat. No. 6,935,167 to Sahin et al. and in 2006/0005614, published Jan. 12, 2006, entitled "Torsional harmonic cantilevers for detection of high frequency force components in atomic force microscopy," both of which are hereby incorporated by reference.

Two examples of harmonic cantilevers are illustrated in the photographs in FIG. 4A and FIG. 4B. As a result of its geometry, the cantilever in 4A has its third flexural resonance frequency at 16 times the first resonance frequency, and the cantilever in 4B has its third flexural resonance frequency at 11 times the first resonance frequency. When harmonic cantilevers are replaced with regular cantilevers and used in tapping-mode AFM they provide all the capabilities of regular cantilevers. However, their primary purpose is to enhance the vibrations at the higher order resonance frequencies that are located at an integer multiple of the first resonance frequency (also the drive frequency).

In FIGS. 1 and 5, vibration spectra obtained with the cantilevers in 4A and 4B when tapping on a silicon wafer with a native oxide surface are given. These two spectrums show peaks at the integer multiples of the drive frequency. The first of these peaks in each spectrum are the highest. Those are the vibrations of the cantilever at the drive frequency and the amplitude of that motion is monitored in the conventional tapping-mode AFM. Other than the first peaks, the two spectrums show relatively good signal levels at the harmonics 16 and 11 in 1 and 5, respectively. These are the high frequency vibrations enhanced by the harmonic cantilevers. These harmonics may be identified by counting the peaks in spectra such as FIG. 1 and FIG. 5, disregarding peaks near the lowest frequencies, which are relatively noisy. The amplitude and phase of these signals can be measured with a lock-in amplifier that locks onto a particular harmonic of the signal at the position sensitive detector. These measurements can be performed while the cantilever is scanned across the surface in tapping-mode AFM. Theoretical and experimental studies have shown that these two quantities depend on the physical properties of sample under test. Therefore, the images generated by recording the amplitude and phase of the enhanced harmonics (referred to elsewhere herein as "stiffness mode") will be mapping material variations, i.e., changes in the elastic properties of the molecules being studied, rather than changes in shape, referred to as topographical mode. The higher harmonic amplitudes are also affected by the attractive forces. While it is not necessary here to properly determine the origin of the contrast, theoretical work showed that it is mainly determined by the stiffness of the sample. Theoretical work on interpreting contrast data is presented in the paper by Sahin, et al., "Resonant Harmonic Response in Tapping-Mode Atomic Force Microscopy" *Phys. Rev. B.* 69 165416 (2004).

The cantilever may also be designed according to US PGPUB 2006/005614, referenced above, as a coupled torsional cantilever. Such a torsional cantilever is illustrated in FIG. 4C. This cantilever is 300 μm long, 30 μm wide and 3 μm thick. FIG. 10 illustrates the use of a coupled torsional cantilever to obtain patterns of tip sample forces on graphite, high-density polyethylene and low-density polyethylene.

The ability to measure higher harmonics of tip-sample forces allows us to reconstruct the periodic tip-sample force waveform. Those frequency components of tip-sample forces that are close to the torsional resonance frequency get enhanced by the resonance. This is seen in a plot of the detector signal against vibration frequency (FIGS. 5B and 5C).

The harmonics that are close to 850 kHz ($16^{th}$ peak) have larger magnitudes. If one is interested in the actual magnitude of the forces, one will correct for the resonance enhancement of the first torsional mode. This is done by sampling the torsional deflection signal at a high sampling rate (with a digital oscilloscope) and then passing it through a linear filter that has a transfer function equal to the inverse of the first torsional mode.

The details of a circuit design incorporating the digital oscilloscope and linear filter will be apparent to those skilled in the art, but further guidance may be found in U.S. Pat. No. 6,137,283 to Williams, et al., issued Oct. 24, 2000 entitled "Process and machine for signal waveform analysis," hereby incorporated by reference.

As further exemplification, torsional oscillations on three different materials (high density polyethylene, low density polyethylene, and highly oriented pyrolytic graphite) were recorded and time resolved tip-sample forces were calculated. The resulting waveforms are given in FIG. 10A. In that figure, negative separation corresponds to sample indentation. The slopes depend on material stiffness. Hysteresis and maximum negative forces depend on the adhesiveness of the sample.

These measurements are recorded under the same drive force, tapping amplitude, and same tip. These waveforms show that tip-sample interaction forces are different for different materials, however interpretation of the differences is difficult. An easy interpretation is provided when these forces are plotted against tip-sample separation (FIG. 10B). Note that the tip is approaching and retracting from the surface in a sinusoidal orbit and the peak forces are obtained when the tip is at the bottom of its trajectory. The slopes of the curves in FIG. 10B at negative separations (sample indentation) are proportional to the stiffness of the sample. As expected, the slope on graphite is higher than the polymers and the slope on the high-density polyethylene is higher than the low-density polyethylene. An interesting feature of these plots is the hysteresis they exhibit. Hysteresis in the force vs. distance plots is a measure of adhesiveness. As a result of attractive forces, compliant materials can be pulled above its equilibrium surface level.

The thermal characteristics of an ultra-thin binary polymer blend film with sub-micron features were also analyzed. The polymer is composed of polystyrene and PMMA. The latter has a higher glass transition temperature. We imaged mechanical properties at the surface at elevated temperatures with our torsional harmonic technique. In this technique, we scan the surface in tapping mode and simultaneously record a particular higher harmonic signal in the torsional spectrum. Higher harmonic imaging has been previously demonstrated with the use of harmonic signals in the flexural response with lower signal to noise levels. The advantage of using torsional harmonics is that one can lock onto any higher harmonic, because all the harmonics provide good signal levels. The information in each harmonic is not the same. At lower temperatures, the two components have similar characteristics. However, as the glass transition temperature of polystyrene is exceeded, we observed a drastic change in the contrast indicating softening in the polystyrene regions. Detailed understanding of the changes is obtained with the measurement of time resolved forces on both materials. Time-resolved force measurements plotted against tip-sample separation on polystyrene and PMMA showed that polystyrene is softening significantly as the temperature is increased, while PMMA does not exhibit detectable changes. These measurements show that polystyrene regions are going through glass transition.

4. Detection of Macromolecular Binding

Figure 6:
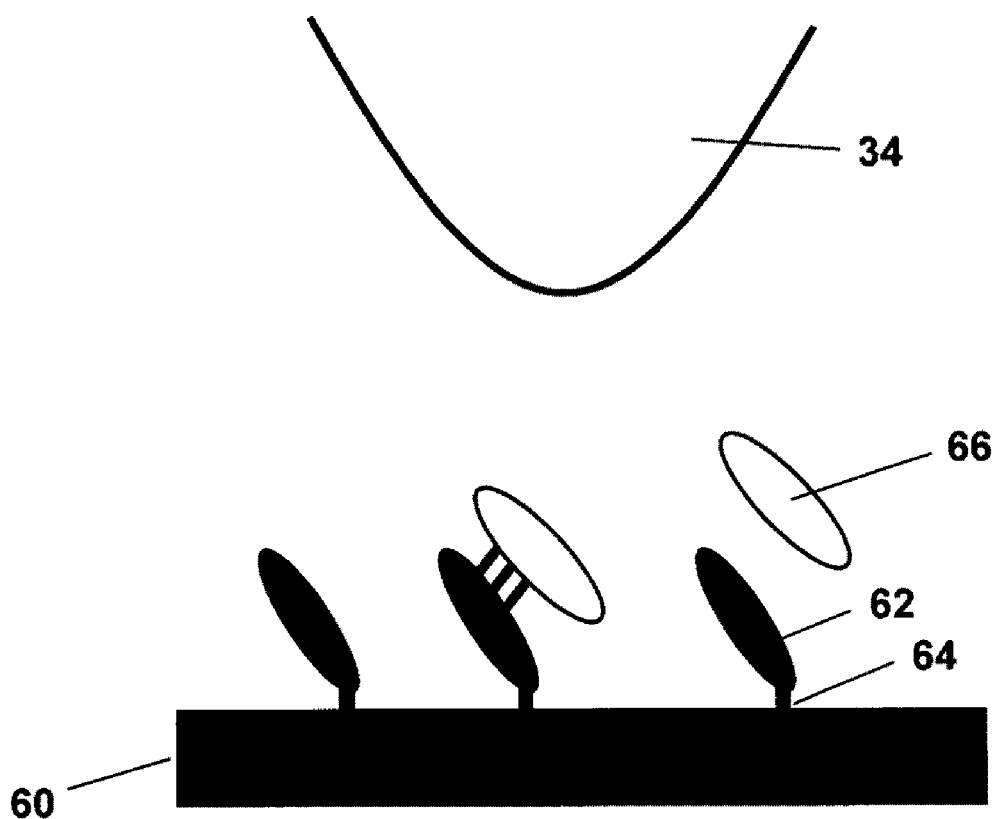
FIG. 6 is a schematic of the AFM tip, DNA molecules, and the surface on which one of the DNA strands are attached.

Referring now to FIG. 6, the present experimental work demonstrates the ability of the harmonic cantilever in stiffness mode to detect and quantify hybridized DNA molecules on a solid surface. In order to detect hybridized DNA molecules with this invention, one begins with a substrate 60 on which single stranded DNA molecules 62 are attached. These substrates with DNA molecules immobilized are commonly used in DNA microarrays and related technologies. The attached DNA molecules of interest are typically 10-60 nucleotides, but may be of any length. The attachment of these molecules can be covalent (e.g., thiolated DNA molecules on gold substrate) or non-covalent. Alternatively, aminated or carboxylated DNA polynucleotides may be covalently immobilized to carboxylated or aminated carbon films via amide bonds by 1-ethyl-3-(3-dimethylaminopropyl) carbodiimide hydrochloride-catalyzed amidation reaction. Alternatively, the covalent attachment of oligonucleotides to silicon(100) surfaces may be accomplished by UV light exposure of hydrogen-terminated silicon(100) coated with alkenes functionalized with N-hydroxysuccinimide ester groups results in Si—C bonded monolayers. The N-hydroxysuccinimide ester surfaces act as a template for the subsequent covalent attachment of DNA oligonucleotides.

According to conventional chemistry for linking nucleic acids, proteins and the like, there will be linker molecules 64 between the first DNA strand and the substrate. Self-assembly of DNA molecules on gold substrates is also commonly used. DNA oligomers synthesized directly on the surface are also commercially used. The samples are placed in a hybridization buffer containing a sample having ss (single stranded) DNA 66, which will hybridize to the immobilized DNA 62 if it is complementary. After the reactions take place, one can scan the surface with a harmonic cantilever in tapping mode AFM and record the amplitude and phase signals at the higher harmonic enhanced by the harmonic cantilever. The cantilever tip 34 is shown as much larger than the diameter of the ds (double stranded) DNA, which is about 2 nm. If some of the molecules are hybridized, the higher harmonic signals will be different at the location of those molecules than the signals on the single stranded molecules.

FIG. 7 shows constructed images from three different samples with end thiolated DNA molecules attached to the gold substrates. These images are obtained by recording the amplitudes of a higher-harmonic signal across a 1-micrometer by 1-micrometer area on each sample in air. The images provide a material property image, representing mainly stiffness. In these images brighter regions correspond to lower vibration amplitudes, i.e. less stiffness. The images in FIG. 7 are believed to represent higher signals on single stranded molecules because we are effectively interacting the stiff gold substrate underneath, however this is not clear nor is it necessary to the design or operation of the present devices. The harmonic cantilever used for this experiment has the design shown in FIG. 4A to match the third resonance frequency to $16^{th}$ multiple of the drive frequency. This cantilever had a spring constant of approximately 1 N/m and quality factor of 75. The set-point amplitude of the vibrations is approximately 70 nanometers whereas the free vibration amplitude is 100 nanometers. Its tip was modified to be hydrophobic using the HMDS vapor prime oven (Yield Engineering Systems Inc., San Jose, Calif.). Using hexamethyldisilazane (HMDS), the unit functions as a standard vacuum vapor primer. The hydrophobic coating (in this case silane) helped to eliminate the attractive capillary forces and simplifies the interpretation of the results.

A tip surface is "hydrophobic" when it displays advancing contact angles for water greater than approximately seventy degrees. In one embodiment, the treated tip the present invention displays advancing contact angles for water between approximately ninety (90) and approximately one hundred and thirty (130) degrees. The present hydrophobic coatings include silane, halogenated silanes and alkylsilanes.

For some macromolecules, it is preferred to use hydrophilic coatings. Hydrophilic polymers such as polyarylene oxides, polyvinylpyrolidones, polyvinylalcohols, hydroxy alkyl cellulosics, algins, saccharides, caprolactones, and the like, and mixtures and combinations thereof may be used, as well as smaller compounds, such as DMSO, as described in U.S. Pat. No. 5,148,311, hereby incorporated by reference. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. A functional moiety may be added to the tip, e.g., those selected from the group consisting of amino, hydroxyl, amido, carboxylic acid and derivatives thereof, sulfhydryl (SH), unsaturated carbon bond and heteroatom bonds, N—COOH, N(C=O)H, S(OR), alkyd/dry resin, formaldehyde condensate, methyol acrylamides and allylic groups (see U.S. Pat. No. 6,866,936).

The image in FIG. 7A shows the gold surface with ssDNA attached. The lighter, spherical objects represent the ssDNA. FIG. 7B shows both ssDNA and hybridized dsDNA, where the macromolecular complexes are seen as larger, bifurcated spots. In FIG. 7C, most of the DNA molecules are double stranded. The scan area is 1 micron by 1 micron.

5. Imaging and Analysis

The first sample, in FIG. 7A, has only single stranded molecules immobilized on it. On the second sample, we immobilized both single and double stranded molecules. Before immobilization on gold, the double stranded molecules and single stranded molecules are mixed such that the percentage of hybridized molecules in the solution is approximately 0.1 percent. On the third sample we immobilized only double stranded molecules. The oligonucleotides of the probes were 25 bases long and the mixed DNA was also 25 bases long. The sequence was artificially designed and chosen to minimize self-hybridization. The images show that signal levels on the fully hybridized sample are largely different than the signal levels on the fully single stranded sample. In the second sample, FIG. 7B, where some of the molecules on the surface are hybridized, we see spots where signal levels are close to those on the fully hybridized sample, also the signal levels on the rest of the surface are close to those on the fully single stranded sample. The values of the signals on each sample are given in FIG. 8. Each graph in this figure corresponds to the signal levels on the lines shown on the corresponding images in FIG. 7. A comparison of the plots in FIG. 8 shows that in the single stranded regions the signal levels are around 0.8-0.9 mV and in the hybridized regions the signal levels drop to 0.4-0.5 mV range. It is important to note that even a single hybridized DNA molecule can potentially be observed with this technique since the resolution is limited with the tip size of the AFM cantilever. However these molecules will appear wider than their physical size due to the convolution of the tip with these structures.

In the presently preferred mode of detecting the presence of bound (e.g., hybridized) molecules on a sample, one can use a harmonic cantilever and record the amplitude or the phase of a higher harmonic vibration signal on that sample and compare these values to a reference sample where one knows that there are hybridized molecules. If one records signal levels close to those obtained on the reference sample, it will tell that there are hybridized DNA molecules on the sample under test. It is important to note that both the reference sample and the test sample needs to be scanned with similar parameters for the free vibration amplitude and set-point amplitude (which will be related to amplitude at the fundamental frequency, the first and largest peaks in FIGS. 1 and 5), and cantilever spring constant, quality factor and index of the harmonic. This is because the response of cantilever vibrations at a higher harmonic depends on these parameters. Based on our experiments and theoretical studies of harmonic cantilever response scanning with a harmonic cantilever that has a spring constant around 1 N/m, quality factor around 75, and an integer ratio between the enhanced harmonic and the first resonance around 8-16 will provide the best contrast for hybridized molecules compared to single stranded molecules. Speed is another factor in the performance of this invention. To improve imaging speed one can use harmonic cantilevers with higher resonance frequencies.

The optimal parameters for cantilever vibration, spring constant and quality factor will also depend on the sample preparation techniques, the choice of substrate, the length of the hybridized region in the DNA molecules. One can find the best parameters on a reference sample and use those parameters on samples with similar properties.

On a sample where both hybridized and single stranded DNA molecules are present one will record primarily two signal levels. One level will belong to hybridized molecules and the other level will belong to single stranded molecules. Therefore, observation of two distinct signal levels is a signature of hybridization. This alternative technique allows one to eliminate the use of a reference sample. However, to detect very small amounts of hybridized molecules one has to keep the contamination at a sufficiently small level. This is because it will be difficult to determine whether the observed signal levels belong to particles contaminating the surface or to hybridized DNA molecules.

An advantage of this invention is the ability to give quantitative values for the number of hybridized molecules on the surface. Since the tip of the AFM is very sharp (2-100 nanometers) it is possible to detect each molecule one by one especially at low surface concentrations. With a computer analyzing the recorded signals one can determine the number of hybridized molecules for a given area. At higher surface concentrations the tip may not be able to resolve two hybridized molecules that are close to each other. In that case one can use a computer to analyze the recorded signals to estimate the area where the signal levels belong to levels for hybridized DNA molecules. This area will be proportional to the density of hybridized molecules on a surface. One can compare the areas covered by hybridized DNA molecules to compare the densities on the two samples.

One can use a sample such as DNA microarrays having a large number (at least 1,000 preferably at least 10,000) discrete nucleic acid locations (spots) and scan the surface with a harmonic cantilever or an array of harmonic cantilevers to determine or quantify the hybridization in each spot of the array. Therefore, this invention can be used instead of conventional techniques that are employed for the read-out of DNA microarrays and similar technologies.

The tapping-mode atomic force microscope may be operated in constant force mode, in which a feedback loop adjusts the cantilever base height so that the amplitude of the cantilever oscillation remains (nearly) constant. The feedback signal reflects the topography of the surface. An image can be formed from the amplitude signal, as there will be small variations in this oscillation amplitude due to the control electronics not responding instantaneously to changes on the specimen surface. Useful imaging technique in tapping-mode is phase imaging. Phase imaging relies on the fact that the tip is driven with $F_o \cos(w_t\text{-phi}_r)$, but the actual response of the tip is $F_o \cos(w_t\text{-phi}_r)$. The phase offset caused by interaction with the surface is then $\text{phi}_d\text{-phi}_r$. Phase is useful because different materials will cause different offsets in phase, due to the fact that it depends on differences in adhesion, friction and viscoelasticity. When the conventional cantilevers used in tapping-mode are replaced with the harmonic cantilevers and coupled torsional cantilevers used as examples in this invention, they will provide additional signals at higher frequencies. These signals are used to map mechanical property variations and images of mechanical properties can be obtained simultaneously with the topography and phase images.

Figure 9:
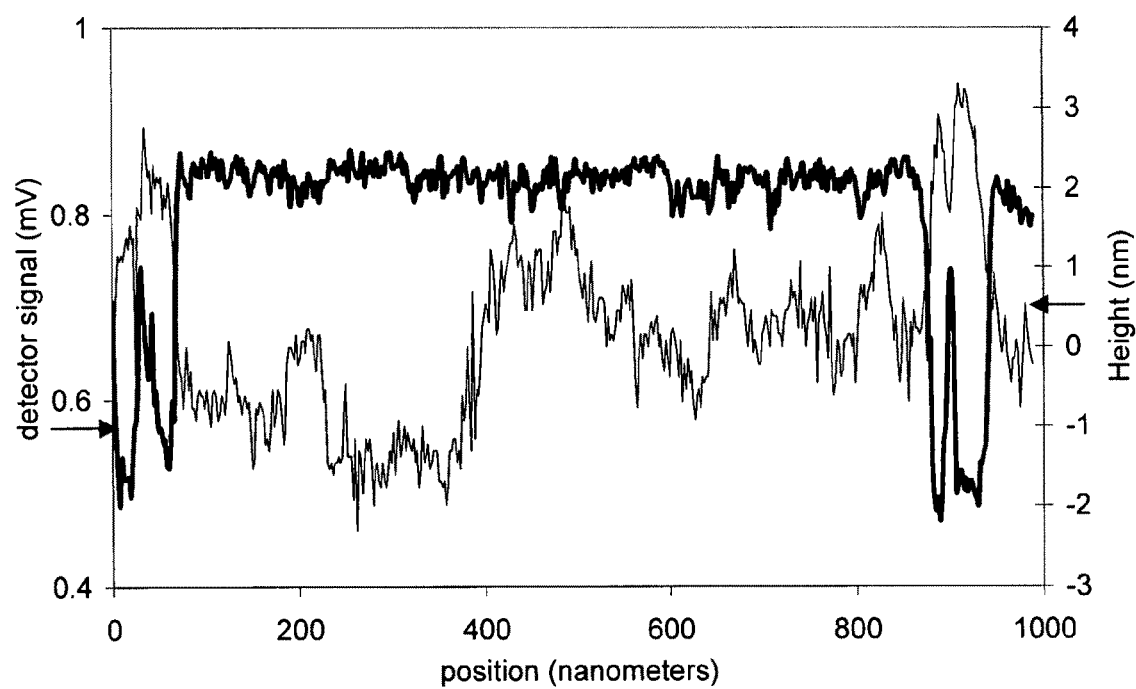
FIG. 9 is a graph of measured vibrational signals showing detector signal (amplitude of the $16^{th}$ harmonic measured with a lock-in amplifier locked onto the $16^{th}$ multiple of the drive frequency.

Non-contact operation is another method that may be employed. The cantilever must be oscillated above the surface of the sample at such a distance that the repulsive regime of the inter-molecular force curve is no loner having significant effect. This is a very difficult mode to operate in ambient conditions with the AFM. The thin layer of water contamination that exists on the surface on the sample will invariably form a small capillary bridge between the tip and the sample and cause the tip to "jump-to-contact." As shown in FIG. 9, however, topographic imaging is not as informative as stiffness measurements. The height signal (light trace) was taken on a sample with 0.1% DNA, analogous to FIG. 8B. This signal is related to the stiffness of the molecules (dark trace) and height (lighter trace). Height signal is generated, as is known, by the feedback signal that adjusts the cantilever height to maintain the vibration amplitude at the set-point level. However, the signal does not indicate with particularity the dsDNA. Thus, the topographic data is not as informative as the higher harmonic amplitude data, which represents stiffness rather than topography. The harmonic signals are unique to the molecules being measured and one can still use the topographical (height) measurement to double-check the measurements to see if the height signal is close to the dimensions of the molecule. This will allow one to eliminate the adverse effects of contaminants present in biological samples.

The harmonic cantilevers and coupled torsional cantilevers enable measurement of variation of tip-sample forces as the vibrating tip approaches, interacts with a molecule and retracts. These forces allow us to access unique mechanical properties of molecules that allow us to detect them specifically, i.e., their mechanical properties as modified by binding to other molecules or themselves. Previous attempts to access biomolecular events involved topographical measurements with AFM to record height variations in molecules, or chemically functionalizing the tip of the AFM to measure chemical forces between the molecules under test and the tip of the AFM. These measurements are tedious and unreliable.

The present description refers to the notion of higher harmonic forces. Higher harmonics are used to represent frequency components of periodic waveforms. Tip-sample forces in tapping-mode atomic force microscope are considered quasi-periodic, that is, during a measurement tip-sample forces can be assumed periodic for practical purposes. In general, harmonic cantilevers and coupled torsional cantilevers can provide information on higher frequency force components that are not necessarily periodic. When the cantilever is scanned across a sample very fast, tip sample forces may not be assumed as quasi-periodic. However, harmonic cantilevers and coupled torsional cantilevers can still allow us to measure variations in tip-sample forces and detect biomolecular interactions, by allowing the measurement of high frequency force components. We still use the notion of harmonics, because it pertains to most practical cases, and, as previously stated, intend that the term "harmonic cantilever" include any measurement of these variations.

6. Preparation and Testing of Ultraflat Surfaces

In this example, a mica substrate is coated with gold to form an ultraflat surface. The term "ultraflat" is known in the art. The ultraflat gold surface is made by depositing gold on to a mica substrate followed by flame-annealing to achieve large ultraflat terraces. See, Lüssem et al, Wagner et al., "The origin of faceting of ultraflat gold films epitaxially grown on mica," *Applied Surface Science*, 249(1-4):197-202 (2005). Flame annealing is further described in U.S. Pat. No. 6,017,590. For further clarity, an ultraflat surface may be considered as having a surface variation of less than about 5 Angstroms. Such ultraflat gold surfaces can also be achieved by an alternative process described by Wagner and coworkers. See, Wagner et al., "Formation and in Situ modification of monolayers chemisorbed on ultraflat template-stripped gold surfaces," *Langmuir*, 11(10):3867-3875 (1995). After any annealing step, the gold is treated with a self-assembling monolayer (SAM), which binds the biomolecules (DNA). The SAM is formed from thiolated alcohols, wherein the thiol group binds the gold. In this case, quartz may be used as a substrate. The hydroxyl terminated SAM is transformed to react with thiolated DNA using known chemistries. Using self-assembled monolayers of substituted alkane thiols as a starting point, other chemistries may be employed, given the present teachings. An exemplary scheme to attach single-stranded DNA molecules to chemically modified gold surfaces is found in U.S. Pat. No. 5,629,213. The term hydroxyl alkane thiol is known in the art. For further clarity it may be defined as has the structural formula HO—$(CH_2)n$-SH where n is between 2 and 20, preferably between 8 and 16.

In addition, the DNA was spotted so that individual samples are closely packed so as to improve sample scanning. The DNA spot separation is between 1 and 10 nm.

5.1. Self-Assembled Monolayers

Sulfur has a strong affinity to metals and solutions containing organosulfur compounds form self-assembled monolayers (SAMs) onto metal substrates. These SAMs are dense and well ordered with the sulfur atoms oriented to the substrate and the tail-group facing away from the metal. Organosulfur compounds used for formation of SAMs include alkanethiols ($HS(CH_2)_n X$), dialkylsulfides ($X(CH_2)_m S(CH_2)_n X$), dialkyldisulfides ($X(CH_2)_m S—S(CH_2)_n)X$), and xanthates ($X(CH_2)_n OC(S)SH$). X represents various reactive groups and m and n are integers representing lengths of alkyl chains and n and m are at least 1, preferably higher. Hydroxy terminated alkanethiols are generally the compound of choice and the order and the stability of the SAM increases with the length of the carbon chain (n) due to increased van der Waals interactions between adjacent carbon chains.

SAMs have been demonstrated on a wide range of metal substrates such as gold, silver, copper, platinum, palladium, nickel, mercury as well as alloys. Nonetheless most studies have been carried out on gold because it is a well-characterized material, inert and compatible with both analytical instruments and biological systems.

Self-assembled monolayers can also be achieved with other compounds such as organosilicon derivatives on oxide surfaces, surfactants on polar surfaces or alkenes on silicon surfaces. However the order of such monolayers is harder to control often resulting in either multilayers or incomplete layers. This makes them a less preferred choice for applications where the control of surface properties is essential.

5. 2. Mica

Mica is a group of sheet silicate minerals with the general formula: $X_2 Y_{4-6} Z_8 O_{20}(OH,F)_4$ in which X is K, Na, or Ca or less commonly Ba, Rb, or Cs; Y is Al, Mg or Fe or less commonly Mn, Cr, Ti, or Li; and Z is chiefly Si or Al but may also include Fe or Ti.

An important characteristic of the mica group of minerals is the almost perfect basal cleavage, caused by the hexagonal sheet-like arrangement of its atoms. This leads to an extremely flat surface, and freshly cleaved mica supporting a thin film of metal is an excellent substrate for studies of SAMs by techniques where surface roughness is of importance. Such films are often made of gold, which is grown epitaxially with an oriented (111) texture on the (100) surface of mica. This results in grain sizes on the order of 1000 nm with flat (111) terraces of up to 100 nm in width. The flatness of the gold surface is often improved by flame annealing the surface after gold deposition. An alternative method for making ultraflat gold substrates is to use template stripping. In this technique a solid support is glued to the exposed surface of a gold film deposited on mica. The gold film is subsequently peeled from the mica resulting in a flat gold surface that is an imprint of the mica surface.

5.3. Gold Substrate

Figure 11:
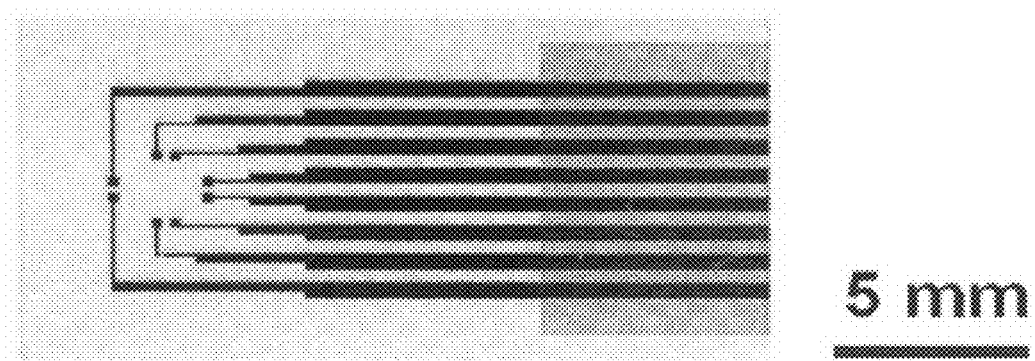
FIG. 11 is a diagram showing a chip configuration for gold substrates (8 electrodes) initially used for DNA immobilization.

Substrates for DNA immobilization were manufactured using a semiconductor-processing technique at the Stanford Nanofabrication Facility. A 1000 Å thick gold layer was deposited on top of a 500 um thick quartz layer using a thin layer of chromium as an adhesion promoter. Two chip configurations were used with either 3 or 8 gold electrodes per chip. One of these chip configurations is shown in FIG. 11.

5.4. Ultraflat Gold-Mica Substrates

Ultraflat Au (111) substrates made from cleaved mica with epitaxially grown and flame annealed gold at least 1500 Å thick were bought from Molecular Imaging. These substrates were cleaned for 15 min in a UV-Ozone cleaner (UVO-42, Jelight, Irvine, Calif.) immediately prior to use.

5.5. DNA-Oligonucleotides

Single-stranded DNA (ssDNA) molecules (25 bases) with different sequences were synthesized at Stanford Genome Technology Center on an Applied Biosystems 3900 synthesizer. Thiolated and biotinylated oligonucleotides were achieved by using either a disulfide or biotin modification on the 5' terminus. All DNA sequences were purified by HPLC and disulfide modified oligonucleotides were reduced with Dithiothreitol (DTT) and desalted twice. All DNA sequences were stored cold and in the dark. The DNA sequences were designed and tested by software to minimize self-hybridization. Oligonucleotides used for experiments had the following sequences:

```
                                       (SEQ ID NO: 1)
A: 5' HS-(CH2)6-TTAAGGTCTGGACTGGCCTGAATTT (SEQ ID NO: 2)
A*: 5'biotin-AAATTCAGGCCAGTCCAGACCTTAA (SEQ ID NO: 3)
B: 5' HS-(CH2)6-ATGCTCATCTAGACAGTATCGGCAC (SEQ ID NO: 4)
B* 5'biotin-GTGCCGATACTGTCTAGATGAGCAT
```

5.6 Other Reagents

All other reagents employed for surface modifications were of reagent grade, and used as received from Aldrich unless otherwise stated.

5.7 SAM Formation on Gold Substrate

The patterned quartz chips were cleaned in an RCA cleaning solution [$H_2O/NH_4OH/30\% H_2O_2$ (5:1:1, vol/vol/vol)] for 15 min at 70° C., immersed in a water bath for 10 min, and dried in a stream of argon. The quartz surface was coated with a hydrophobic octadecyltriethoxysilane (Gelest, Morrisville, Pa.) in an anhydrous toluene solution containing 1% (vol/vol) silane and 2% (vol/vol) hexanoic acid for 24 h at room temperature. Silanized chips were washed twice with toluene and once with ethanol for 5 min each and dried in a stream of argon. The silanization step was performed to make the quartz surface hydrophobic and thereby avoid cross-contamination between gold electrodes in close proximity to each other during spotting. Subsequently the gold electrodes were coated with a long-chain thiol that forms a densely packed monolayer and displaces any physisorbed silanes. The silane-coated chips were immersed immediately in a 1 mM solution of mercaptoundecanol ($HO(CH_2)_{11} SH$) in ethanol for at least 12 h. The gold substrates were removed from the thiol solution, washed with ethanol, and dried under an argon stream.

The hydroxyl-terminated monolayer was transformed into a thiol-reactive moiety by exposure to a 2.3 mM solution of N-(p-maleimidophenyl) isocyanates (Pierce, Rockford, Ill.) in anhydrous toluene at 40° C. for 2 h under an argon atmosphere. Maleimide-modified gold electrodes were washed with anhydrous toluene and dried in a stream of argon.

5.8 SAM Formation on Ultraflat Gold-Mica Substrates

Ultraflat gold-mica substrates surfaces cleaned for 15 min in UV-Ozone were immersed in a 1 mM solution of mercaptoundecanol in ethanol for at least 12 h. The gold substrates were removed from the thiol solution, washed with ethanol, and dried under an argon stream. The hydroxyl-terminated monolayer was transformed into a thiol-reactive moiety by exposure to a 2.3 mM solution of N-(p-maleimidophenyl) isocyanates (Pierce, Rockford, Ill.) in anhydrous toluene at 40° C. for 2 h under an argon atmosphere. Maleimide-modified gold electrodes were washed with anhydrous toluene and dried in a stream of argon.

5.9 DNA Immobilization and Hybridization on Thiol-reactive SAMs

The thiolated oligonucleotides (A and B) were mixed in ratios ranging from 1:0 (100% A) down to 1:1000 (0.1% A) and diluted to final combined DNA concentrations of 0.5-20 uM in 0.01 M phosphate buffered saline (PBS), pH 7.4. Thiolated DNA mixtures were spotted onto a thiol-reactive monolayer and incubated in a chamber with controlled humidity for at least 12 h. After DNA immobilization the gold substrates were washed extensively with PBS, dried in a stream of Argon and incubated with 1 mM Mercaptohexanol (MCH) for 1 h in phosphate buffer. After incubation with MCH the gold substrates were washed several times with buffer solution, once with deionized water and dried in a stream of argon.

A 5-20 uM solution of complementary DNA (A*) in PBS was spotted onto the DNA immobilized gold substrates, covered with a glass coverslip and allowed to hybridize for at least 16 h under humidity control. After DNA hybridization the gold substrates were washed several times with PBS, once with deionized water and dried in a stream of argon. Samples were stored at ambient conditions until analysis.

5.10 Direct Immobilization of Pre-hybridized DNA onto Ultraflat Gold-Mica Substrates Thiolated oligonucleotide (A) was mixed with a 10% stoichiometric excess of complementary DNA (A*), heated to 70° C., cooled down to room temperature and allowed to hybridize for at least 1 h. The pre-hybridized mixture was mixed with thiolated oligo (A) in ratios from 1:0 (100% double-stranded DNA, dsDNA) to 1:1000 (0.1% dsDNA) and diluted in phosphate buffered saline with a total salt concentration varying from 0.15M to 1.2 M. The total concentration of thiolated oligonucleotide (A) was kept constant at 20 uM.

Thiolated DNA mixtures were spotted onto ultraflat gold-mica substrates and incubated in a chamber with controlled humidity at 37° C. for at least 12 h. After immobilization of pre-hybridized DNA, the gold substrates were washed extensively with buffer solution and dried in a stream of argon. This was followed by incubation with 1 mM Mercaptohexanol (MCH) at 37° C. for 1 h in phosphate buffer. After incubation with MCH the gold substrates were washed several times with buffer solution, once with deionized water and dried in a stream of argon. Samples were stored at ambient conditions until analysis.

5.11. SAM Formation, DNA Immobilization and Hybridization on Gold Substrates

Figure 12:
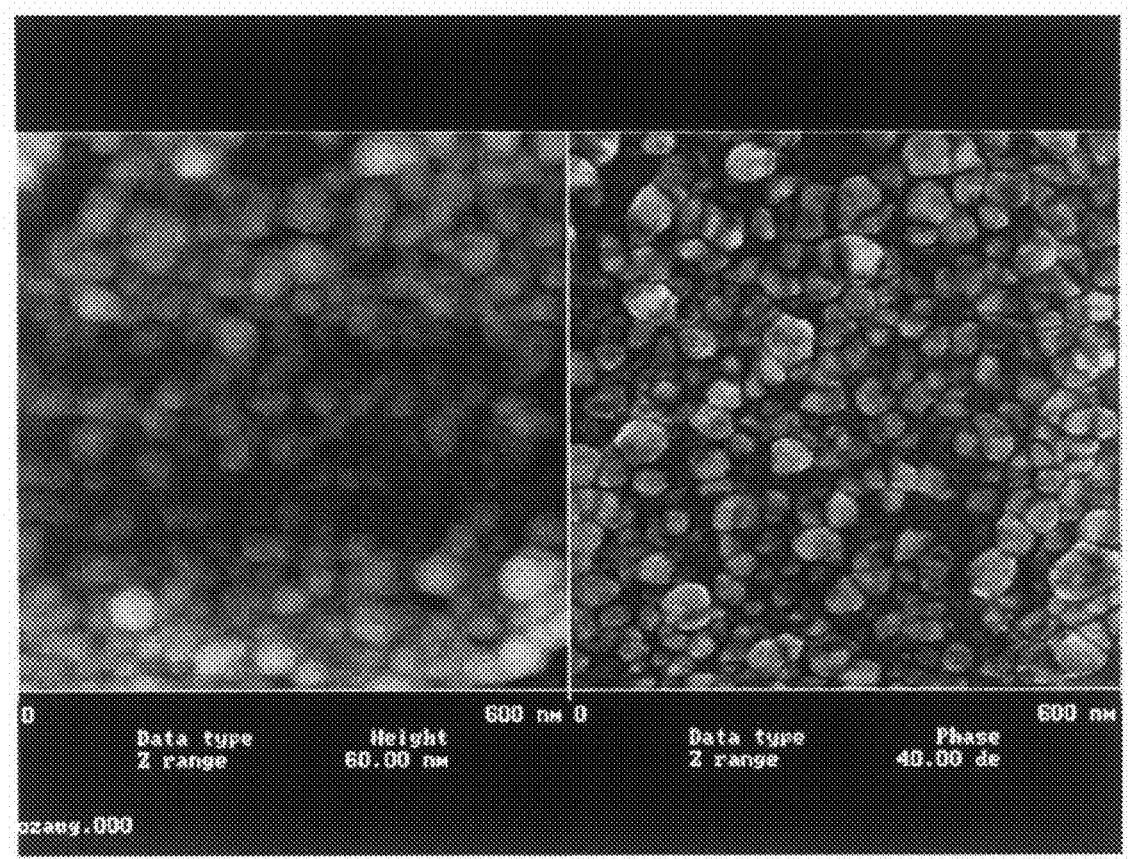
FIG. 12 is a photograph showing a gold substrate after monolayer formation, DNA immobilization and hybridization.

Using gold substrates described in section 5.7 or 6.7 and immobilization procedures described above, an image of gold substrates after monolayer formation, immobilization of DNA and hybridization with complementary DNA was obtained, as shown in FIG. 12. The edgy features seen in the image are believed to be the grain boundaries of deposited gold. If the height difference between the gold grains are on the same size or larger than the length of the DNA molecules they will perturb the imaging of DNA molecules and accordingly no traces of DNA could be found in the image. This led us to assume that it would be very difficult to see any hybridization on these substrates and it was the main motivation for switching to the ultraflat gold substrate.

Figure 13:
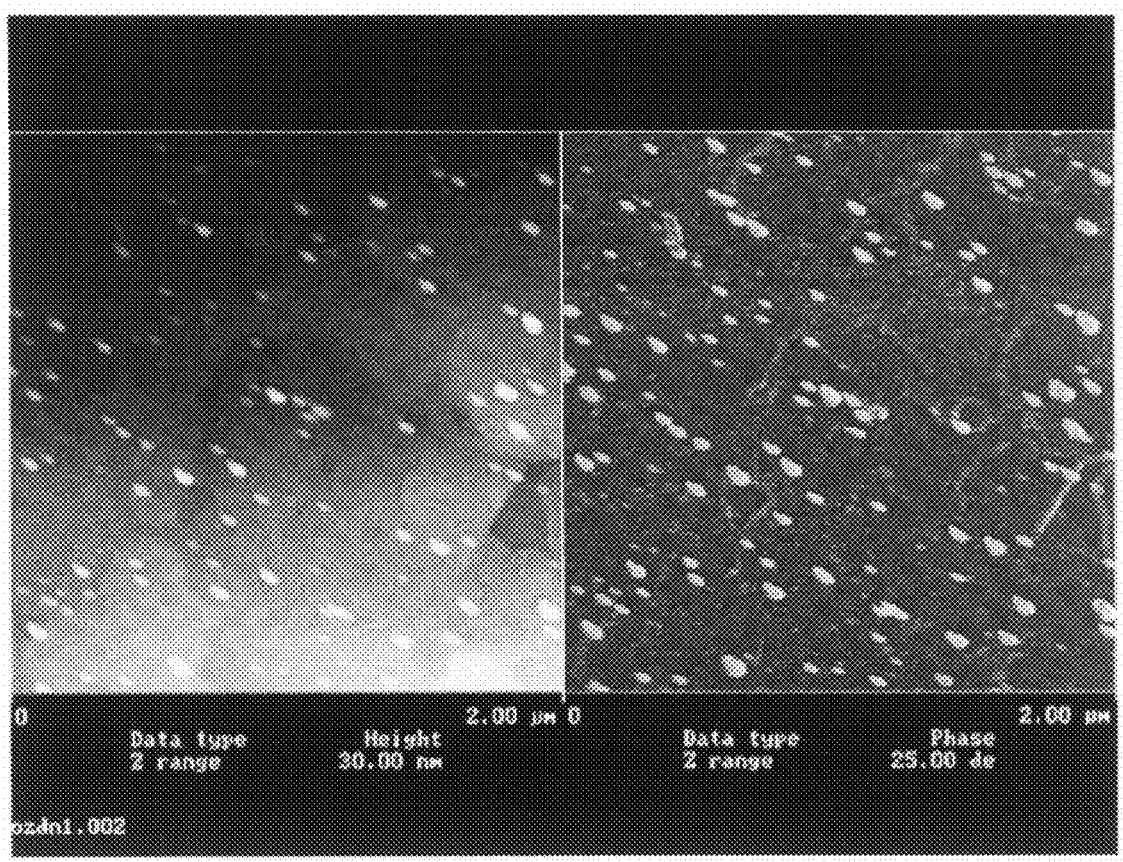
FIG. 13 is a photograph showing an ultraflat gold-mica substrate after formation of a self-assembled monolayer, DNA immobilization (10% DNA sequence A and 90% DNA sequence B) and hybridization with DNA sequence A*.

5.12 SAM Formation, DNA Immobilization and Hybridization on Ultraflat Gold-Mica Substrates Using ultraflat gold-mica substrates described in section 5.2. and immobilization procedures described in section 5.8 and 5.9, an image of an ultraflat gold-mica substrate after monolayer formation, immobilization of DNA (10% A and 90% B), and hybridization with complementary DNA (A*) was obtained as shown in FIG. 13. The discrete features seen in the figure are assumed to be individual DNA molecules after hybridization. The coarse grain boundaries found in FIG. 12 cannot be seen anymore. A few grain boundaries are however dimly visible in the topography image on the left in FIG. 13. The results of these experiments were encouraging and demonstrated the potential of using harmonic cantilevers for detection of hybridized DNA. However, in order to facilitate single and double stranded sample preparation, the alternative sample preparation described in below was developed. That is, the DNA was pre-hybridized with defined amounts of a complementary strand, so that the resulting microscopic images could be correlated to expected amounts of ss and ds DNA.

5.13 Direct Immobilization of pre-hybridized DNA on Ultraflat Gold-Mica Substrates Using ultraflat gold-mica substrates described in section 5.2 and immobilization procedures described in section 5.10, images were obtained as shown in FIG. 7. The upper part shows a surface of pure ssDNA(100% A), the middle part is a surface containing a mixture of both ssDNA and pre-hybridized dsDNA, and the lower part shows a surface of pure dsDNA (100% A-A*). Clear differences can be seen between the images and the amount of bifurcated spots increases with the concentration of pre-hybridized dsDNA. These spots are believed to be individual molecules of dsDNA duplexes. The distance between the spots in the bottom of FIG. 7 is on the order of 10-100 nm and can be altered by varying the salt concentration of the buffer solution from which the DNA molecules are adsorbed. A higher ionic strength will shield the negative charge of neighboring DNA molecules, minimize electrostatic repulsions, and thereby decrease the distance between DNA molecules. The salt concentration can thus be altered to tailor the distance between neighboring DNA molecules so that the cantilever can resolve individual duplexes of dsDNA as seen in the lower part of FIG. 7.

CONCLUSION

The present examples, methods, procedures, specific compounds and molecules are meant to exemplify and illustrate the invention and should in no way be seen as limiting the scope of the invention, which is defined by the literal and equivalent scope of the appended claims.

For example, as discussed above, the invention is not limited to DNA molecules. Furthermore, the DNA molecules exemplified herein may be other polynucleic acids. Natural nucleic acids have a phosphate backbone; artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of a tRNA (transfer RNA), snRNA (small nuclear RNA), rRNA (ribosomal RNA), mRNA (messenger RNA), antisense RNA, and ribosymes. DNA may be in form plasmid DNA, viral DNA, linear DNA, or chromosomal DNA or derivatives of these groups. In addition these forms of DNA and RNA may be single, double, triple, or quadruple stranded. The term also includes PNAs (peptide nucleic acids), phosphothionates, and other variants of the phosphate backbone of native polynucleic acids.

The polynucleotides to be contacted and measured here may be labeled, unlabelled, or linked to other reporter molecules.

Any patents or publications mentioned in this specification are indicative of levels of those skilled in the art to which the patent pertains and are intended to convey details of the invention which may not be explicitly set out but would be understood by workers in the field. Such patents or publications are hereby incorporated by reference to the same extent as if each was specifically and individually incorporated by reference and for the purpose of describing and enabling the method and apparatus referred to.

What is claimed is:

1. A method for distinguishing individual single-stranded DNA molecules from individual double-stranded DNA molecules, wherein said individual single-stranded DNA molecules and said individual double-stranded DNA molecules are disposed on discrete locations on a substrate, comprising the steps of:
   preparing a sample substrate having a gold surface with DNA molecules deposited thereon in discrete locations;
   vibrating a harmonic cantilever with a tip and obtaining a harmonic signal from said vibrating;
   contacting the vibrating harmonic cantilever tip with the sample substrate comprising said DNA molecules at said discrete locations;
   measuring changes in said harmonic signal at different sample DNA molecules in different discrete locations; and
   measuring changes in said harmonic signal in order to distinguish individual single-stranded DNA molecules from individual double-stranded DNA molecules,

SEQUENCE LISTING

<160> NUMBER OF SEQ ID NOS: 4

<210> SEQ ID NO 1
<211> LENGTH: 25
<212> TYPE: DNA
<213> ORGANISM: artificial
<220> FEATURE:
<223> OTHER INFORMATION: synthetic test equence

<400> SEQUENCE: 1
ttaaggtctg gactggcctg aattt                                          25

<210> SEQ ID NO 2
<211> LENGTH: 25
<212> TYPE: DNA
<213> ORGANISM: artificial
<220> FEATURE:
<223> OTHER INFORMATION: synthetic test sequence

<400> SEQUENCE: 2
aaattcaggc cagtccagac cttaa                                          25

<210> SEQ ID NO 3
<211> LENGTH: 25
<212> TYPE: DNA
<213> ORGANISM: artificial
<220> FEATURE:
<223> OTHER INFORMATION: synthetic test sequence

<400> SEQUENCE: 3
atgctcatct agacagtatc ggcac                                          25

<210> SEQ ID NO 4
<211> LENGTH: 25
<212> TYPE: DNA
<213> ORGANISM: artificial
<220> FEATURE:
<223> OTHER INFORMATION: synthetic test sequence

<400> SEQUENCE: 4
gtgccgatac tgtctagatg agcat                                          25 wherein said individual single-stranded DNA molecules and individual double-stranded DNA molecules produce harmonic signals that differ in one or both of amplitude and phase.

2. The method of claim 1 wherein the sample comprises a mixture of single-stranded and double-stranded nucleic acids hybridized prior to deposition.

3. A method for distinguishing individual single-stranded DNA molecules from individual double-stranded DNA molecules, comprising:
- disposing different samples of single-stranded DNA molecules and double-stranded DNA molecules at discrete locations on a sample substrate comprising gold with linker molecules between a first DNA strand and the substrate;
- contacting a vibrating harmonic cantilever tip with said individual single-stranded DNA molecules and individual double-stranded DNA molecules at each of said discrete locations to obtain a signal at a harmonic frequency representing deflection of the cantilever tip;
- measuring changes in said signal at different single-stranded DNA molecules and double-stranded DNA molecules in different discrete locations; and
- measuring changes in said signal in order to distinguish an individual single-stranded DNA molecule from an individual double-stranded DNA molecule by measuring harmonic signals that differ in one or both of amplitude and phase.

4. The method of claim 1 wherein said DNA molecules deposited on a gold surface are thiolated.

* * * * *